US012653660B2

(12) United States Patent
Kashintsev et al.

(10) Patent No.: US 12,653,660 B2
(45) Date of Patent: Jun. 16, 2026

(54) CATHETER AND METHOD FOR ISOLATING A REGION IN A HOLLOW ORGAN OF A MAMMAL, AND SYSTEM BASED ON THE CATHETER, AND USE OF THE CATHETER

(71) Applicant: PANDICA LTD, England (GB)

(72) Inventors: Aleksei Arievich Kashintsev, Saint-Petersburg (RU); Vitali Yurievich Proutski, Saint-Petersburg (RU); Sergey Vladimirovich Anisimov, Saint-Petersburg (RU); Oleg Konstantinovich Granstrem, Saint-Petersburg (RU)

(73) Assignee: PANDICA LTD, England (GB)

( * ) Notice: Subject to any disclaimer, the term of this patent is extended or adjusted under 35 U.S.C. 154(b) by 883 days.

(21) Appl. No.: 17/790,320

(22) PCT Filed: Dec. 28, 2020

(86) PCT No.: PCT/RU2020/050399
§ 371 (c)(1),
(2) Date: Jun. 30, 2022

(87) PCT Pub. No.: WO2021/137739
PCT Pub. Date: Jul. 8, 2021

(65) Prior Publication Data
US 2023/0037101 A1 Feb. 2, 2023

(30) Foreign Application Priority Data

Dec. 31, 2019 (RU) .............................. RU020100187
Dec. 9, 2020 (RU) ........................... RU2020140524

(51) Int. Cl.
*A61F 2/04* (2013.01)
*A61M 25/10* (2013.01)
*A61B 17/00* (2006.01)

(52) U.S. Cl.
CPC ...... *A61F 2/04* (2013.01); *A61B 2017/00818* (2013.01); *A61F 2002/041* (2013.01)

(58) Field of Classification Search
CPC .............. A61M 25/1011; A61M 25/10; A61M 25/1002; A61M 25/1006; A61M 25/1009;
(Continued)

(56) References Cited

U.S. PATENT DOCUMENTS 4,781,677 A 11/1988 Wilcox
5,222,941 A 6/1993 Don Michael
(Continued)

FOREIGN PATENT DOCUMENTS

RU 2607929 C2 11/2017
WO 01/19445 A1 3/2001
(Continued)

OTHER PUBLICATIONS

European Patent Office, International Search Report issued in International Patent Application No. PCT/RU2020/050399, mailed Jun. 10, 2021 (5 pages).
(Continued)

*Primary Examiner* — Majid Jamialahmadi
(74) *Attorney, Agent, or Firm* — The Marbury Law Group, PLLC

(57) ABSTRACT

Catheters for isolating an interior of a mammal hollow organ, each comprising: (i) an elongate catheter body designed to be inserted into a lumen of the mammal hollow organ; (ii) two balloons individually and separately disposed along the catheter body and designed to be inflated to isolate the interior of the mammal hollow organ therebetween; and (iii) a functional channel extending in the catheter body and comprising a functional opening provided in the catheter body between the balloons; wherein the functional channel is designed to allow a negative pressure to be produced in
(Continued)

the isolated interior to take a liquid or gaseous medium therefrom via the functional opening or allow a liquid or gaseous medium to be supplied to the isolated interior via the functional opening.

18 Claims, 4 Drawing Sheets

(58) Field of Classification Search
CPC ........ A61M 25/104; A61M 2025/1095; A61M 2025/1004; A61M 2025/1013; A61M 2025/1015; A61B 2017/00818; A61F 2/958; A61F 2002/9583
See application file for complete search history.

(56) References Cited

U.S. PATENT DOCUMENTS

| | | | |
|---|---|---|---|
| 5,314,409 A | 5/1994 | Sarosiek et al. | |
| 5,397,305 A | 3/1995 | Kawula et al. | |
| 5,460,610 A | 10/1995 | Don Michael | |
| 5,658,264 A | 8/1997 | Samson | |
| 5,843,050 A | 12/1998 | Jones et al. | |
| 5,919,163 A | 7/1999 | Glickman | |
| 5,951,514 A * | 9/1999 | Sahota ............... | A61M 25/1011 |
| | | | 604/101.05 |
| 6,638,245 B2 | 10/2003 | Miller et al. | |
| 6,692,465 B2 | 2/2004 | Kramer | |
| 6,712,798 B2 | 3/2004 | Constantz | |
| 7,070,606 B2 | 7/2006 | Seward | |
| 7,722,568 B2 | 5/2010 | Lenker et al. | |
| 8,398,589 B2 | 3/2013 | Teeslink et al. | |
| 9,526,874 B2 | 12/2016 | Teeslink et al. | |
| 10,009,865 B2 | 6/2018 | Islam et al. | |
| 2003/0176830 A1 | 9/2003 | Scheule | |
| 2015/0150572 A1 | 6/2015 | Kumbhari et al. | |

FOREIGN PATENT DOCUMENTS

| | | |
|---|---|---|
| WO | 2009/035581 A1 | 3/2009 |
| WO | 2018106788 A1 | 6/2018 |
| WO | 2021137739 A1 | 7/2021 |

OTHER PUBLICATIONS

European Patent Office, International Preliminary Report on Patentability, issued in International Application No. RU2020/050399, dated Mar. 24, 2022 (9 pages).
National Cancer Comprehensive Network, "Pancreatic Adenocarcinoma" NCCN Clinical Guidelines in Oncology (NCCN Guidelines®), Version 3, 156 pages, (Jul. 2, 2019).
Martinez-Noguera, et al., "Ultrasound of the pancreas: update and controversies", Eur. Radiol. 11: pp. 1594-1606, (Jul. 11, 2001).
Iglesias-Garcia, et al., "Endoscopic ultrasound elastography", Department of Gastroenterology and Foundation for Research in Digestive Diseases (FIENAD), Spring Publishing, vol. 1, Issue 1, 9 pages, (2001).
Hruban, et al., "An Illustrated Consensus on the Classification of Pancreatic Intraepithelial Neoplasia and Intraductal Papillary Mucinous Neoplasms", Am J. Surg. Pathol., vol. 28, No. 8, pp. 977-987, (Aug. 2004).
Ogawa, et al., "A Case of Small Pancreatic Cancer with Intrapancreatic Metastasis Diagnosed by Endoscopic Ultrasound", Tokai J. Exp. Clin. Med., vol. 36, No. 3, pp. 75-78, (2011).
Kawaguchi, et al., "Randomized controlled trial of pancreatic stenting to prevent pancreatitis after endoscopic retrograde cholangiopancreatography", World Journal of Gastroenterology, vol. 18 (14), pp. 1635-1641, (Apr. 14, 2012).
Suenaga, et al., "Using an endoscopic distal cap to collect pancreatic fluid from the ampulla", Gastrointest Endosc., 86 (6), pp. 1152-1156, (Dec. 2017).

Kanda, et al., "Mutant TP53 in Duodenal Samples of Pancreatic Juice from Patients with Pancreatic Cancer or High-Grade Dysplasia", Clin Gastroenterol Hepatol., 11 (6), pp. 719-730, (Jun. 2013).
Akisik, et al., "Dynamic Secretin enhanced MR Cholangiopancreatography", RadioGraphics, vol. 26, No. 3, pp. 665-677, (May-Jun. 2006).
Hanada, et al., "Roles of ERCP in the Early Diagnosis of Pancreatic Cancer", Diagnostics, 9, 30, doi. 10.3390/diagnostics9010030, www.mpdp.com/journal/diagnostics, 10 pages, (2019).
Budzinsky, et al., "Endoscopic transpapillary pancreatic stenting in the treatment of pancreatic fistulas" (with a commentary by A.G. Krieger), Journal named after N.I. Pirogov., (2), pp. 32-44, (2017).
Stevens, et al., "A prospective crossover study comparing secretin-stimulated endoscopic and Dreiling tube pancreatic function testing in patients evaluated for chronic pancreatitis", Gastrointestinal Endoscopy, vol. 67, No. 3. pp. 458-466, (2008).
Pollack, et al., "Where Have All the Dreiling Tubes Gone?", American Journal of Gastroenterology, Am Coll. of Gasterenterology, 101 (2), pp. 356-359, (2006).
Osnes, et al., "Comparison of Juice Obtained during Duodenal Aspiration and Cannulation of the Main Pancreatic Duct after Stimulation with Exogenous Secretin in man", Scand J Gastroenterol. 13 (4), pp. 453-458, (1978).
Minami, et al., "Clinical Usefulness of Serial Pancreatic-Juice Aspiration Cytological Examination and Endoscopic Ultrasound-Guided Fine-Needle Aspiration in Small Pancreatic Cancer", 152, Issue 5, Supplement 1, p. S897, (Apr. 2017).
Bi, et al., "How to suction pancreatic juice from the duodenum: Endoscope, catheter, or cap-assisted?" vol. 86, No. 6, Gastrointestinal endoscopy, www.giejournal.org, pp. 1157-1159, (2017).
Go, et al., "Simultaneous measurements of total pancreatic, biliary, and gastric outputs in man using a perfusion technique", Gastroenterology, vol. 58, No. 3, pp. 321-328, (1970).
Burgart, "Cholangitis in Viral Disease", Mayo Clinic Proceedings, V. 73 (5), pp. 479-482, (May 1998).
Brunt, "Liver Biopsy Diagnosis of Hepatitis: Clues to Clinically-Meaningful Reporting", Missouri Medicine, 107 (2), pp. 113-118, (Mar./Apr. 2010).
Dumonceau, et al., "Prophylaxis of post-ERCP pancreatitis: European Society of Gastrointestinal Endoscopy (ESGE) Guideline—updated Jun. 2014", Endoscopy, 46 (9), pp. 799-815, (2014).
Smotrin, "Obturating agents for treating gastrointestinal fistulas", Journal of the State Medical University for Practicing Physicians, No. 4, (2007).
Bobkiewicz, et al., "Management of enteroatmospheric fistula with negative pressure wound therapy in open abdomen treatment: a multicenter observational study", International Wound Journal ISSN, 1742-4801, 14 (1): pp. 255-264, (Feb. 2017).
Anjiki, Endoscopic hemostasis techniques for upper gastrointestinal hemorrhage: A review:, World J Gastrointest Endosc., 2 (2), pp. 54-60, Feb. 16, 2010.
Roszelle, et al., "Comparison Among Different High Porosity Stent Configurations: Hemodynamic Effects of Treatment in a Large Cerebral Aneurysm", Journal of Biomechanical Engineering, vol. 136 (2): 021013, 10 pages, (Feb. 2014).
Ozimok, et al., "An international survey to assess use of oral and rectal contrast in CT protocols for penetrating torso trauma", Emergency Radiology, https://doi.org/10.1007/s10140-018-1650-7, 26 (2), pp. 117-121, (Apr. 2019).
Broder, et al. "Emergency department contrast practices for abdominal / pelvic computed tomography—a national survey and comparison with the American college of radiology appropriateness criteria", The Journal of Emergency Medicine, vol. 44, No. 2, pp. 423-433, (2013).
Beger, et al., "The Pancreas, an Integrated Textbook of Basic Science, Medicine and Surgery", table of contents, Third edition, Blackwell. UK. 1300, 11 pages, (2018).
European Patent Office, Written Opinion of the International Searching Authority cited in related International Application No. PCT/RU2020/050399, mailed Jun. 10, 2021, 7 pages.
European Patent Office, International Preliminary Report on Patentability (Annex), issued in International Application No. RU2020/050399, dated Dec. 19, 2021, 54 pages.

(56) References Cited

OTHER PUBLICATIONS

D'Hondt, et al., "Treatment of small-bowel fistulae in the open abdomen with topical negative-pressure therapy", The American Journal of Surgery, 202, pp. e20-e24, (2011).

Budzinsky, et al., "Endoscopic pancreatic stenting in pancreatic fistulas management" Scientific-educational center of abdominal surgery and endoscopy N.I. Pirogov RSMU, Municipal clinical hospital No. 31, Moscow Russian Federation; doi: 10/17116/hirurgia2017232-44, (2017).

Hocmynura, 616.34-007.253-089, , p. 160-163, (Nov. 7, 2020).

Udod, VM, et al., "Obturator for temporary closure of a gastrointestinal fistula," USSR AS 764685, M. class A 61 M 27/00, by application 2723792/28-13, declared Dec. 22, 1978, BIO 35. (Sep. 23, 1980).

International Search Report and Written Opinion from the European Patent Office cited in related International Application No. PCT/RU2021/000477, mailed Jan. 5, 2023 (5 pages).

Written Opinion of the International Searching Authority received from the European Patent Office in corresponding International Application No. PCT/RU2021/000477 dated May 4, 2023 (7 pages).

* cited by examiner

CATHETER AND METHOD FOR ISOLATING A REGION IN A HOLLOW ORGAN OF A MAMMAL, AND SYSTEM BASED ON THE CATHETER, AND USE OF THE CATHETER

FIELD OF THE INVENTION

The present invention relates to medicine, and more particularly to medical equipment used to diagnose, monitor and/or treat inflammatory, autoimmune, infectious, benign and/or malignant diseases, that occur in hollow organs and connected with them organs of a mammal, in particular diseases of pancreas, bile ducts, liver, gastrointestinal tract, and also defects and injuries of hollow organs of a mammal, fistulas, strictures, aneurismal and diverticular dilatations, and other diseases of the hollow organs. In particular, the present invention relates to catheters and a system for isolating an interior of a mammal hollow organ that have an improved safety.

BACKGROUND

Known in the art are various devices and appliances used to diagnose and/or treat inflammatory, autoimmune, infectious, benign and/or malignant diseases that occur in hollow organs of a mammal, in particular diseases of pancreas, bile duct diseases, liver diseases, and also gastrointestinal wall defects, injuries of the wall of a hollow organ, aneurismal and diverticular dilatation, strictures of hollow organs, bleeding of hollow organs and some other diseases of hollow organs, and diseases of organs connected to hollow organs.

According to guidelines for diagnosing and treating a pancreatic cancer, main techniques allowing for a histological type of neoplasm to be confirmed are fine-needle percutaneous core-biopsy, fine-needle functional biopsy, cytological analysis of an epithelial scraping (also referred to in the art as a brush-biopsy), diagnostic laparoscopy with a biopsy, and cytological analysis of washings obtained from an abdominal cavity during laparoscopy or laparotomy (Pancreatic adenocarcinoma guidelines. National Cancer Comprehensive Network. 2019 Version 2.2019). These officially recommended biopsy techniques are based on different principles, and therefore they cannot be regarded as the closest prior art for the present invention.

In particular, known in the art is an ultrasonic method for studying pancreas (Minko A. B. Complex beam diagnostics of pancreas diseases/A. B. Minko, B. C. Pruchansky, L. I. Korytova. —SPb: Hippokrat, 2001. —134 p.; Martínez-Noguera A., Montserrat E., Torrubia S., et al., 2001) Ultrasound of the pancreas: update and controversies. Eur Radiol 11: 1594-1606). The ultrasonic method is based on the assessment of changes in the reflection and absorption of waves from an organ tissue and allows for gland contours, liver contours and alternations of hyperechoic or hypoechoic zones to be determined. Furthermore, the ultrasonic method allows for determination a Wirsung duct formation and its diameter, a bile duct formation and its diameter, and other formations and their diameters. The main disadvantage of an ultrasonic method is in that examination result depends on a specialist's qualification and an apparatus' resolution. In this case, the sensitivity of the ultrasound examination is 70-80%. If a size of the formation is less than 1.5 cm, the ultrasonic method has strongly reduced effectiveness. In particular, the ultrasonic method does not allow for intraductal neoplasms to be detected, the pancreatic duct to be completely evaluated, a biochemical composition of pancreatic juice and bile to be evaluated, and pancreatic juice and bile to be cytologically examined.

Furthermore, known in the art is a method of endoscopic ultrasound examination based on the same principle as the above-described ultrasonic method (see Ogawa M., Kawaguchi Y., 2011, Iglesias-Garcia J., 2012). An advantage of the endoscopic ultrasound examination over the ultrasonic method is in that biopsy may be performed in close proximity to a site of interest. A convex probe, if any, allows for a suspicious formation to be examined with a fine-needle functional biopsy followed by a cytological examination. Disadvantages of the endoscopic ultrasound examination are the following: necessity to have a highly skilled specialist, necessity to perform anesthetic aid, high costs, and lack of possibility to perform examination in some cases due to some anatomical features. Furthermore, endoscopic ultrasound examination is not suitable for performing cytologic diagnostics of liver and of bile ducts and allows only for a small amount of cytological material to be obtained by performing aspiration, so that it is difficult to interpret the obtained cytological material, causing a high proportion of false-positive results and false-negative results. Furthermore, the endoscopic ultrasound examination does not allow for a qualitative analysis of the composition of bile or pancreatic juice.

Furthermore, known in the art is a fine-needle biopsy, wherein the fine-needle core-biopsy is always used in combination with the above-described ultrasonic method and the above-described endoscopic ultrasound examination and allows for a material for histological examination to be obtained (Hruban R. H., Takaori K., Klimstra D. S. An illustrated consensus on the classification of pancreatic intraepithelial neoplasia and intraductal papillary mucinous neoplasms. Am J. Surg. Pathol. 2004. V. 28 (8) P. 977-87). The fine-needle biopsy is a main method used to histologically verify pancreatic diseases. Disadvantages of the fine-needle biopsy are possible complications: bleeding, formation of fistulas, abscesses, dissemination of cancer cells along a puncture channel, and also uninformative, false-positive or false-negative results of histocytological examinations. Furthermore, the fine-needle biopsy is not suitable for diagnosing diseases of the bile ducts and gallbladder and does not allow for the laboratory evaluation of bile or pancreatic juice.

Furthermore, known in the art is a method of spiral computer-assisted tomography with an intravenous contrast (MSCT) (Callery M. R. et al., 2009; Klaub M. et al., 2009). The spiral computer-assisted tomography is based on the computer-assisted processing of thin "slice" tomograms, assessment of the degree of absorption of a contrast agent by the tissue of a gland or tumor, and the measuring of a diameter of the ducts. The spiral computer-assisted tomography allows for the visualization of formations and making a decision on whether an acute or chronic inflammatory change of corresponding organ is observed based on changes in organ densitometric parameters. Disadvantages of the spiral computer-assisted tomography are significant decrease in its sensitivity when the formation's size is less than 1.5 cm, and low sensitivity and specificity when diagnosing intraductal neoplasms. Furthermore, spiral computer-assisted tomography does not allow for a disease to be histologically confirmed and does not allow for pancreatic secretion to be analyzed.

Furthermore, known in the art is an endoscopic retrograde cholangiopancreatography (ERCP) method (Kawaguchi Y., Ogawa M., Omata F. Randomized controlled trial of pancreatic stenting to prevent pancreatitis after endoscopic retrograde cholangiopancreatography. World Journal of Gastroenterology 2012. Vol. 18 (14). P. 1635-1641). In the endoscopic retrograde cholangiopancreatography, focal formations and calculi are revealed in the form of filling defects. Disadvantages of the endoscopic retrograde cholangiopancreatography are the need for anesthetic aid, a number of limitations preventing certain manipulations, and injuries associated with the procedure, potentially causing destructive pancreatitis or acute cholangitis.

Furthermore, known in the art is an endoscopic aspiration method for aspirating pancreatic juice from duodenum interior by stimulating excretory function of pancreas with Chirhostim™, which is a synthetical analogue of secretin (Suenaga M., Sadakari Y., Almario J. A., et al. Using an endoscopic distal cap to collect pancreatic fluid from the ampulla. Gastrointest Endosc. 2017; 86 (6): 1152-1156; Kanda M., Sadakari Y., Borges M., et al. Mutant TP53 in Duodenal samples of pancreatic juice from patients with pancreatic cancer or high-grade dysplasia. Clin Gastroenterol Hepatol. 2013; 11 (6): 719-730). The endoscopic aspiration method is used for sampling a material followed by cytological examination and/or molecular genetic analysis thereof. Disadvantages of the endoscopic aspiration method are as follows: lack of public acceptance, and limitation of the amount of sampled pancreatic secretion by duration of drug's action by short duration of the procedure. It is of note that composition of pancreatic juice may change when secretin or its analogues is administered, so that the sampled pancreatic secretion in this case does not have its natural composition, and therefore it is not impossible to evaluate the real composition and secretion clearance of pancreatic juice since the function is stimulated by the drug. The endoscopic aspiration method is also not suitable for collecting and analyzing bile.

Furthermore, known in the art is a magnetic resonance imaging (MRI) method used for determining neoplasms and inflammatory changes of pancreas and/or bile ducts (Akisik M F, Sandrasegaran K., Aisen A A Dynamic secretin enhanced MR cholangiopancreatography. RadioGraphics. 2006. Vol. 26. P. 665-677). The magnetic resonance imaging is a non-invasive method and provides an increased sensitivity and specificity when used in combination with radiographic opacification or stimulation of excretory function of pancreas. The disadvantage of the magnetic resonance imaging is the impossibility of evaluating a composition and clearance of bile or pancreatic juice and performing cytological examination thereof.

Furthermore, known in the art is a method of performing a nasopancreatic or nasobiliary drainage followed by the isolated sampling of a substrate (Handa K., Minami T., Shimizu A., et al. Roles of ERCP in the Early Diagnosis of Pancreatic Cancer. Diagnostics 2019, 9 (1), 30; Budzinsky S. A., Shapovalyants S. G., Fedorov E. D., Shabrin A. V. Endoscopic transpapillary pancreatic stenting in the treatment of pancreatic fistulas (with a commentary by A. G. Krieger). Journal named after N. I. Pirogov. 2017; (2): 32-44). The nasopancreatic or nasobiliary drainage is used both for treating inflammatory pancreatic diseases and for performing their cytological verification, wherein the nasopancreatic or nasobiliary drainage is suitable for compositional analysis of biofluids. Furthermore, the nasopancreatic or nasobiliary drainage is a single method allowing for pancreatic juice and bile to be independently sampled. A disadvantage of the nasopancreatic or nasobiliary drainage is the complexity of implementation. For the first time, the use of the nasopancreatic or nasobiliary drainage was described in 1980, however the nasopancreatic or nasobiliary drainage is not a routine method and used only in highly specialized institutions, in particular for solving a limited range of tasks, primarily for treating acute pancreatitis. In some cases, particularly due to the presence of some anatomical features, the nasopancreatic or nasobiliary drainage may not be implemented and may cause various complications such as pancreatitis, cholangitis and bleeding.

Furthermore, known in the art is a two-channel Dreiling tube used for performing duodenal intubation (Stevens T., Conwell D L, Zuccaro G., et al. A prospective crossover study comparing secretin-stimulated endoscopic and Dreiling tube pancreatic function testing in patients evaluated for chronic pancreatitis. Gastrointestinal Endoscopy. 2008. 67 (3). P. 458-466; Pollack B J, Grendell J H. Where have all the dreiling tubes gone? Am J Gastroenterol. 2006 February; 101 (2): 356-nine). The Dreiling tube allows for a non-invasive sampling of pancreatic juice and bile followed by a biochemical test and/or cytological examination thereof and by determination of daily clearance. A disadvantage of the Dreiling tube is that it does not allow for the selective sampling of the content of duodenum, leading to the retrograde sampling of intestinal contents. The passive nature of sampling of excreta leads to its partial loss in distal sections due to the peristalsis of duodenum. However, it is of note that passive positioning of the tube, achieved by the weight of the olive in a distal part of the tube and peristalsis of gastrointestinal tract, leads to excessive time required for positioning of the tube and the need to perform radiographic correction of its position, wherein it is difficult to provide an appropriate positioning of the tube's channels for sampling pancreatic juice and bile. The use of stimulating drugs, such as, for example, secretin, cannot be regarded as an adequate solution since they only increase the bicarbonate buffer excretion provided by cells of the pancreas, i.e. only the activity of the epithelial cells covering the ducts is stimulated, and most of the exocrine gland apparatus remains inactive. Therefore, the Dreiling probe does not allow for stimulation of the function of adenocarcinomas, mucinous neoplasms and neuroendocrine tumors. Furthermore, the Dreiling tube is an alternative to the endoscopic retrograde cholangiopancreatography and may be used only to diagnose chronic pancreatitis, wherein intraductal mucinous and cystous formations and carcinomas cannot be revealed in situ by using the Dreiling tube. Furthermore, when the Dreiling tube is used, it is quite difficult to evaluate the choleresis due to the passage of a part of bile or pancreatic juice through the duodenum beside the Dreiling tube.

Furthermore, known in the art is a nasopancreatic stent inserted into the main duct of pancreas by using an endoscopic technique (Osnes M., Petersen H., Schrumpf E. Comparison of juice obtained during duodenal aspiration and cannulation of the main pancreatic duct after stimulation with exogenous secretin in man. Scand J Gastroenterol. 1978; 13 (4): 453-8; Minami T., Hanada K., Hirano N., et al. Clinical Usefulness of Serial Pancreatic-Juice Aspiration Cytological Examination and Endoscopic Ultrasound-Guided Fine-Needle Aspiration in Small Pancreatic Cancer. 152, Issue 5, Supplement 1, Page S897; Bi Y., Ji B., Raimondo M. How to suction pancreatic juice from the duodenum: Endoscope, catheter, or cap-assisted No. 86 (6). 2017 Gastrointestinal endoscopy. P. 1157-1159). During an endoscopic papilosphincterotomy, the nasopancreatic stent allows a probe to be inserted and, therefore, allows for pancreatic secretion to be obtained. The disadvantage of the nasopancreatic stent is its traumatic nature, leading to the development of pancreatitis, cholangitis or obstructive jaundice. In 3-10% of cases, an endoscopic retrograde cholangiopancreatography may cause acute pancreatitis, so that in this case all patients have to go through a special preventive therapy. Furthermore, during the papilosphincterotomy, a large vessel may be damaged, thereby causing bleeding. It is to note that the nasopancreatic stent may be used only in highly specialized centers by a specialist experienced with the procedure.

Furthermore, known in the art is a dual-lumen duodenal probe inserted through a nasal passage under control of an endoscope, allowing for the duodenal probe to be advanced through a pyloroduodenal area (Bi Y., Ji B., Raimondo M. How to suction pancreatic juice from the duodenum: Endo-scope, catheter, or cap-assisted? 86 (6). 2017 Gastrointesti-nal endoscopy. P. 1157-1159; Go V L, Hofmann A F, Summerskill W H. Simultaneous measurements of total pancreatic, biliary, and gastric outputs in man using a perfusion technique. Gastroenterology 1970; 58: 321-328). A disadvantage of the duodenal probe is the impossibility of selective sampling of pancreatic juice and bile, and lack of a barrier for mixing of the excreta with intestinal and gastric contents, which leads to activation of pancreatic enzymes and digestion of biological material in the probe. Further-more, it is of note that design of the duodenal probe does not allow one to influence the outflow of pancreatic juice from the pancreas, so that in order to obtain the juice and perform its examination, pancreas has to be stimulated by drugs such as secretin.

Furthermore, known in the art is a pancreatic juice aspi-ration device designed to aspirate pancreatic juice by using an endoscope formed as a cap fitted on a fibroscope, wherein the cap allows for the pancreatic secretion to be collected after stimulation of the organ's exocrine function (Suenaga M, Sadakari Y, Almario J A, et al. Using an endoscopic distal cap to collect pancreatic fluid from the ampulla (with video. Gastrointest Endosc 2017; 86: 1152-1156). Disadvantages of the aspiration device are as follows: the complexity of the procedure since it can be implemented only in highly specialized centers, and a small amount of the collected pancreatic secretion (wherein the available amount of pan-creatic secretion is a critical aspect of a molecular test). In this case, the procedure based on the use of the aspiration device is performed by using anesthetic aid, wherein the procedure cannot be performed for a long time.

Known in the art is a method of diagnosing viral hepatitis in blood by using serological and molecular genetic meth-ods. Nevertheless, in 20% of cases, a disease remains unverified since it is conditioned by a life cycle of a virus and by its tropism both to hepatocytes and to the epithelium of the bile ducts, causing viral cholangitis and the disease chronization (Shakhgildyan I. V., Mikhailov M. I., Onishchenko G. G. Parenteral viral hepatitis (epidemiology, diagnosis, prevention). Moscow: GOU VUNMTS MZ RF, 2003; Burgart L J Cholangitis in Viral Disease. Mayo Clinic Proceedings; 1998. V. 73 (5); 479-482). The diagnostic method does not allow for obtaining a bile for further laboratory analysis.

Known in the art is a method of diagnosing diseases of the liver (viral hepatitis, autoimmune hepatitis, sclerosing cho-langitis, liver tumors) by performing a percutaneous biopsy followed by histological and molecular genetic analysis (Bunt E M Liver Biopsy Diagnosis of Hepatitis: Clues to Clinically-Meaningful Reporting. Mo Med. 2010; 107 (2): 113-118). In some cases, such a method leads to complica-tions (bleeding, biliary peritonitis). At the same time it does not allow one to reveal pathologic changes in about 30% of cases. Furthermore, such a method is used exclusively for primary diagnostics, and practically never used repeatedly, for example for monitoring the dynamics or development and progression of a disease.

Furthermore, known in the art is a method of treating acute pancreatitis by stenting the main pancreatic duct to restore the efflux of enzymes of the pancreas. Such a method is used for treating and preventing pancreatitis after per-forming the endoscopic retrograde cholangiopancreatogra-phy (Mozharovsky V. V., Mutnykh A. G., Zhukov I. N., Mozharovsky K. V. Stenting of the main pancreatic duct influences the treatment results obtained for patients with an acute pancreatitis. Surgery. Journal named after N. I. Pirogov. 2019; (9): 13-17; Dumonceau J M., Andriulli A., Elmunzer B J., et al. Prophylaxis of post-ERCP pancreatitis: European Society of Gastrointestinal Endoscopy (ESGE) Guideline—updated June 2014. Endoscopy. 2014 Septem-ber; 46 (9): 799-815). A disadvantage of the method is in that stenting procedure can be performed only in highly special-ized centers, wherein in some cases the procedure cannot be performed at all due to anatomical features of a mammal duct system. Furthermore, the procedure does not solve the problem of pancreatitis due to the disruption of the outflow of pancreatic juice associated with paresis of duodenum.

Furthermore, intestinal fistulas occur on average in 1-3% of patients after performing operations on abdominal cavity organs (Smotrin I. S. Obturating agents for treating gastro-intestinal fistulas. Journal of the State Medical University for Practicing Physicians. —2007. —No. 4). The overall mortality associated with this pathology ranges from 16.5% to 57.5%, and the postoperative mortality associated with this pathology ranges between 10% and 21.4%, wherein the greatest mortality is observed for disembodied intestinal fistulas and ranges between 36% and 71.7%. The mortality barely reaches 4% for embodied intestinal fistulas.

Known in the art is a method of treating gastrointestinal fistulas by using systems for producing a negative pressure, wherein the method is based on the constant evacuation of all pathologic discharge from abdominal cavity, thereby healing defects (Bobkiewicz A, Walczak D, Smolinski S. et al. Management of enteroatmospheric fistula with negative pressure wound therapy in open abdomen treatment: a multicenter observational study. Int Wound J. 2017 Febru-ary; 14 (1): 255-264; D'Hondt M., Devriendt D., Van Rooy F. et al. Treatment of small-bowel fistulae in the open abdomen with topical negative-pressure therapy. Am J Surg. 2011; 202 (2): e20-4). Furthermore, in case when the method is used, statistics collected by the same authors indicate that such defects are not closed (not healed) in 30-47% of cases due to contents constantly produced and received from a lumen of a mammal hollow organ.

Furthermore, there are a large number of different obtu-rator-like devices aimed at disconnecting the lumen of a mammal hollow organ with a defect in a wall. However great variety of such devices suggests the difficulty of their implementation and achieving desired effects. Furthermore, all such well-known devices are aimed only at disconnecting the lumen of the mammal hollow organ with the wall defect and do not aim to impact an area adjacent to the wall defect (Vitsyn B. A., Blagitko E. M. Formed and unformed external intestinal fistulas. —Novosibirsk: Nauka. —1983. —142 p.; Makarenko T. P., Bogdanov A. V. Gastrointestinal fistulas. —M.: Medicine. —1986. —144 pp. USSR AS 764685, M. class A 61 M 27/00. Obturator for temporary closure of a gastrointestinal fistula/V M Udod and E. G. Karsten. By application 2723729/28-13. Declared 12/22/78. Publ. 09/23/ 80. BI 35).

Known in the art are methods of treating gastrointestinal hemorrhages that are based on the usage of endoscopic methods, clipping, ligation, injection of sclerosants or vasoactive drugs into the mucosal layer, and also coagulation using thermal and electrical methods (Anjiki H, Kamisawa T, Sanaka M, Ishii T, Kuyama Y. Endoscopic hemostasis techniques for upper gastrointestinal hemorrhage: A review. World J Gastrointest Endosc. 2010; 2 (2): 54-60). Furthermore, in case of bleeding from a putrescent tumor, necrotizing esophagitis or nonspecific erosive colitis, i.e. in case when the diffuse mucosa bleeding occurs without an obvious source, such known methods remain ineffective, while they also do not allow for objective control of stability of hemostasis.

Known in the art is a method of diagnosing aneurismal dilatations of vessel by administering intraluminal endovascular catheters with or without stents, involving guiding the catheter under control of a fluoroscopy and obturating an aneurism with a stent (Roszelle B N, Nair P, Gonzalez L F, Haithem Babiker M, Ryan J, Frakes D. Comparison among different high porosity stent configurations: hemodynamic effects of treatment in a large cerebral aneurysm. J Biomech Eng. 2014 February; 136 (2): 021013). However, if this known method is implemented, during the positioning of a catheter in a correct manner and identifying a defect, a circumferential blood flow may suffer, and hemorrhage from an aneurysm cavity may continue. Therefore existing analogues differ from the claimed technique.

Known in the art is a method for detecting injuries of mammal hollow organs by administering various coloring or radiopaque substance into the mammal hollow organ (Ozimok C J, Mellnick V M, Patlas M N. An international survey to assess use of oral and rectal contrast in C T protocols for penetrating torso trauma. Emerg Radiol. 2019 April; 26 (2): 117-121; Broder J S, Hamedani A G, Liu S W, Emerman C L. Emergency department contrast practices for abdominal/pelvic computed tomography—a national survey and comparison with the american college of radiology appropriateness criteria (J Emerg Med. 2013 February; 44 (2): 423-33). However, the manipulation itself only allows an injury to be ascertained, wherein this is not always possible since the success of ascertaining an injury strongly depends on the location of an injury and specifics of administration of a substance. In other words, this known method does not always allow for an injury of a hollow organ to be accurately located and does not allow for treatment of this injury.

A similar catheter for isolating an interior of a mammal hollow organ is disclosed in U.S. Pat. No. 9,526,874 published on 30 Jun. 2015. The catheter disclosed in U.S. Pat. No. 9,526,874 comprises an elongate catheter body designed to be inserted into a lumen of a mammal hollow organ and two isolating balloons designed to be inflated to isolate the interior of the mammal hollow organ therebetween; and a functional channel extending in the catheter body and comprising a functional opening provided in the catheter body between the isolating balloons, wherein the functional channel is designed to allow: a negative pressure to be produced in the isolated interior to take therefrom a biological fluid being specific to the hollow organ or a liquid or gaseous medium to be supplied into the isolated interior.

A disadvantage of the catheter disclosed in U.S. Pat. No. 9,526,874 is in that it cannot be inserted into a lumen of a mammal hollow organ for a long time due to the lack of physiological connectivity between hollow organ sections adjoining the hollow organ interior isolated by the inflated isolating balloons and being outside the isolated interior of the mammal hollow organ.

Other similar catheters for isolating an interior of a mammal hollow organ are disclosed in U.S. Pat. No. 4,781, 677 published on 1 Nov. 1988, U.S. Pat. No. 5,460,610 published on 24 Oct. 1995, international publication No. 2018106788 published on 14 Jun. 2018, U.S. Pat. No. 5,951,514 published on 14 Sep. 1999 and U.S. Pat. No. 5,222,941 published on 29 Jun. 1993.

A main disadvantage of the catheter as disclosed in U.S. Pat. Nos. 478,167, 5,460,610, WO 2018106788 or U.S. Pat. No. 5,222,941 is in that the functional opening of the catheter body may be quickly blocked or occluded with a tissue of the mammal hollow organ and/or a material related to the catheter body or catheter structural components and, thus, the catheter cannot be used in the mammal hollow organ for a long time, and the mammal hollow organ in turn may be damaged.

The closest prior art to the present invention is a catheter disclosed in U.S. Pat. No. 5,951,514 (IPC: A61M 29/00; publication date: 14 Sep. 1999). The catheter disclosed in U.S. Pat. No. 5,951,514 has the same disadvantage as the above-mentioned catheters disclosed in U.S. Pat. Nos. 478, 167, 5,460,610, WO 2018106788 and U.S. Pat. No. 5,222, 941.

Therefore, catheters and a system for isolating an interior of a mammal hollow organ are to be further developed, in particular to prevent the functional opening of the catheter body from being blocked or occluded with a hollow organ tissue of the mammal hollow organ and, therefore, to prevent the mammal hollow organ from being damaged when using the catheter within the mammal hollow organ.

Consequently, a main technical problem to be solved by the present invention is to develop catheters and a system for isolating an interior of a mammal hollow organ that would at least partly eliminate the above disadvantage of the prior art, i.e. to eliminate the problem of blockage or occlusion of the functional opening with a hollow organ tissue that may cause damage to the mammal hollow organ during use of the catheter.

SUMMARY OF INVENTION

An objective of the present invention is to develop catheters and a system for isolating an interior of a mammal hollow organ that would solve at least the above-mentioned main technical problem.

To achieve the objective of the present invention, as embodied and broadly described herein, in a first aspect of the present invention, there is provided a catheter for isolating an interior of a mammal hollow organ, the catheter comprising: (i) an elongate catheter body designed to be inserted into a lumen of a mammal hollow organ; (ii) two balloons, individually and separately disposed along the catheter body and designed to be inflated to isolate the interior of the mammal hollow organ therebetween; and (iii) a functional channel extending in the catheter body and comprising a functional opening provided in the catheter body between the balloons, wherein the functional channel is designed to allow: (a) a negative pressure to be produced in the isolated interior to take a liquid or gaseous medium therefrom via the functional opening or a liquid or gaseous medium to be supplied into the isolated interior via the functional opening, wherein the catheter body is further provided with a net or enclosure being permeable to a liquid medium and/or gaseous medium, and wherein the net or enclosure at least partly encloses a catheter body part defined by the balloons so as to cover the functional opening, and wherein the net or enclosure is attached to the balloons or encloses them such that the net or enclosure becomes strained when the balloons are inflated.

A main technical effect provided by the catheter according to the first aspect of the present invention is improved safety of the catheter due to prevented suction of a hollow organ tissue of the mammal hollow organ (e.g. a mucosal tissue of the mammal hollow organ) into the functional opening of the catheter body that would otherwise cause damage to the hollow organ tissue. In particular, in the catheter according to the first aspect of the present invention, suction of the hollow organ tissue into the functional opening is prevented due to the fact that the net or enclosure in the strained state covers the functional opening and displaces the hollow organ tissue for a predetermined distance away from the functional opening, wherein the prevented suction of the hollow organ tissue into the functional opening of the catheter body allows the safety of the catheter to be improved. Moreover, the safety of the catheter according to the first aspect of the present invention is further improved due to the fact that the net or enclosure in the strained state redistributes the pressure from the inflated balloons on an inner wall of the mammal hollow organ and, therefore, prevents pressure related lesions in the inner wall. Besides, the safety of the catheter according to the first aspect of the present invention is further improved due to the fact that the net or enclosure in the strained state pulverizes or sprays the liquid or gaseous medium be supplied into the isolated interior and, therefore, prevents the inner wall of the mammal hollow organ from being intensively effected by a flow of the supplied liquid or gaseous medium that would otherwise damage the effected inter wall site of the mammal hollow organ.

Another technical effect provided by the catheter according to the first aspect of the present invention is increased reliability of the catheter due to prevented partial or complete blockage or occlusion of the functional opening that may be caused by suction of a tissue of the mammal hollow organ into the functional opening, thereby preventing the inserted catheter from being retrieved from the mammal hollow organ and, then, changing the retrieved catheter to a new catheter or removing the hollow organ tissue sucked into the functional opening from the functional opening of the retrieved catheter. In particular, in the present invention according to the first aspect, suction of the hollow organ tissue into the functional opening is prevented due to the fact that the net or enclosure in the strained state covers the functional opening.

In one of embodiments of the present invention according to the first aspect, the catheter may further comprise an inflation channel extending in the catheter body to deliver a liquid or gaseous medium to the balloons to provide inflation thereof. Delivery of the liquid or gaseous medium to the catheter balloons through the inflation channel for inflating the balloons provides a further technical effect which is a combination of simplified maintenance of balloon sizes as required to isolate the interior of the mammal hollow organ and simplified regulation of sizes or inflation degrees of the catheter balloons.

In another embodiment of the present invention according to the first aspect, the catheter comprising the inflation channel may further comprise a second channel extending in the catheter body and hermetically isolated from the functional channel and the inflation channel, wherein the second channel may be provided at opposite ends thereof with an inlet and an outlet which are provided both in the catheter body outside the catheter part defined by the balloons, and wherein the second channel may be further designed to supply a liquid thereto and may be further provided with an additional outlet, the additional outlet being provided at a catheter distal end used for inserting the catheter into the lumen of the mammal hollow organ.

A further technical effect provided by the second channel of the catheter body is the provision of liquid medical products or the provision of an enteral nutrition mixture, the enteral nutrition mixture providing a mammal organism with basic nutrients, energy, vitamins, macronutrients, micronutrients and/or etc., to an interior of the mammal hollow organ via the additional outlet while sampling a biological liquid medium or biological gaseous medium from the isolated interior of the mammal hollow organ via the functional opening.

Another technical effect provided by the second channel of the catheter body is prevented or excluded formation of congestive and/or inflammatory processes which would occur in the mammal hollow organ due to the accumulation of mucus and other biological contents being specific to the mammal hollow organ outside the catheter body part defined by the balloons. In particular, the formation of congestive and/or inflammatory processes in the mammal hollow organ is prevented or excluded due to the fact that mucus and other biological contents being specific to the mammal hollow organ, when accumulated in the mammal hollow organ, may enter the inlet provided in the catheter body outside the catheter body part defined by the balloons, and may leave through the outlet provided in the catheter body outside the catheter body part defined by the balloons.

Moreover, the above-described positive effects provided by the additional outlet provided at the catheter distal end in combination with the above-described positive effects provided by the inlet and the outlet provided both in the catheter body allow the catheter according to the first aspect of the present invention to be inserted into the lumen of the mammal hollow organ for a long time.

Furthermore, the hermetical isolation of the second channel from the functional and inflation channels in the catheter according to the first aspect of the present invention provides a further technical effect which is in that the liquid supplied to the second channel and/or the mucus and other biological contents entering the inlet of the second channel are prevented from entering the functional channel and inflation channel. Thus, a biological liquid medium or biological gaseous medium taken via the functional opening in the functional channel is prevented from mixing with said liquid supplied to the second channel and/or with the mucus and other biological contents entering the inlet of the second channel that would otherwise negatively influence the reliability or representativity of laboratory-instrumental analysis results obtained for the biological liquid medium or biological gaseous medium. Also, the liquid medium or inflation medium used to inflate the balloons is prevented from mixing with said liquid supplied to the second channel and/or with the mucus and other biological contents entering the inlet of the second channel that would otherwise negatively influence the inflation degree of the balloons and, therefore, impair the isolation of the mammal hollow organ.

In another embodiment of the present invention according to the first aspect, each of the functional channel and inflation channel may be hermetically isolated from each other. The hermetically isolated functional and inflation channels in the catheter according to the first aspect of the present invention provide a further technical effect which, in particular, is in that the liquid or gaseous medium used to inflate the balloons is prevented from entering the functional channel and, therefore, a biological liquid medium or biological gaseous medium taken via the functional opening in the functional channel is prevented from mixing with said inflation medium that would otherwise negatively influence the reliability or representativity of laboratory-instrumental analysis results obtained for the biological liquid medium or biological gaseous medium.

In some embodiments of the present invention according to the first aspect, two ring-shaped projections enclosing the functional opening may be further provided on the catheter body between the balloons such that the functional opening may be between said ring-shaped projections and adjacent thereto. The ring-shaped projections enclosing the functional opening provided in the catheter body provide a further technical effect which is prevented suction of a hollow organ tissue, in particular a mucosal tissue of a hollow organ, into the functional opening since the ring-shaped projections do not allow the functional opening to constant directly with the tissue or approach the tissue for a distance appropriate for suction thereof when the negative pressure is produced in the hollow organ interior isolated by the inflated catheter balloons.

To achieve the objective of the present invention, as embodied and broadly described herein, in a second aspect of the present invention, there is provided a catheter for isolating an interior of a mammal hollow organ, the catheter comprising: (i) an elongate catheter body designed to be inserted into a lumen of the mammal hollow organ; (ii) two balloons, individually and separately disposed along the catheter body and designed to be inflated to isolate the interior of the mammal hollow organ therebetween; and (iii) a functional channel extending in the catheter body and comprising a functional opening provided in the catheter body between the balloons, wherein the functional channel is designed to allow a negative pressure to be produced in the isolated interior to take a liquid or gaseous medium therefrom via the functional opening or a liquid or gaseous medium to be supplied into the isolated interior via the functional opening, and wherein two ring-shaped projections enclosing the functional opening are further provided on the catheter body between the balloons such that the functional opening is between the two ring-shaped projections, and wherein the two ring-shaped projections are both designed such that they allow a distance between a mucosal tissue of the mammal hollow organ, the mucosal tissue being between the inflated balloons, and the functional opening to be provided when the negative pressure is produced.

The catheter according to the second aspect of the present invention provides the main technical effect mentioned above for the catheter according to the first aspect of the present invention, in particular improves safety of the catheter due to prevented suction of a tissue of the mammal hollow organ into the functional opening of the catheter body that would otherwise cause damage to the hollow organ tissue. In particular, in the present invention according to the second aspect of the present invention, suction of the hollow organ tissue into the functional opening is further prevented due to the fact that the functional opening provided in the catheter body is between the ring-shaped projections enclosing the functional opening. In other words, in the present invention according to the second aspect, the ring-shaped projections enclosing the functional opening do not allow the hollow organ tissue to contact the functional opening directly or approach to the functional opening for a distance appropriate for suction of the hollow organ tissue into the functional opening when the negative pressure is produced in the isolated interior between the inflated balloons.

The catheter according to the second aspect of the present invention provides the further technical effect mentioned above for the catheter according to the first aspect of the present invention, in particular increases reliability of the catheter due to prevented partial or complete blockage or occlusion of the functional opening that may be caused by suction of a tissue of the mammal hollow organ into the functional opening (i.e. suction of the hollow organ tissue into the functional opening is further prevented due to the fact that the ring-shaped projections enclose the functional opening provided in the catheter body, and the functional opening is between the ring-shaped projections), thereby preventing the inserted catheter from being retrieved from the mammal hollow organ and, then, changing the retrieved catheter to a new catheter or removing the hollow organ tissue sucked into the functional opening from the functional opening of the retrieved catheter.

Furthermore, the catheter according to the second aspect of the present invention provides a first new technical effect which is extended or increased volume of the isolated interior of the mammal hollow organ, the isolated interior being used for producing the negative pressure therein. In particular, the extended or increased volume of the isolated interior of the mammal hollow organ is provided by the catheter according to the second aspect of the present invention due to the fact that the projections enclosing the functional opening are ring-shaped. The extended or increased volume of the isolated interior of the mammal hollow organ allows a controlled negative pressure to be produced in the isolated interior, the negative pressure having a level required to provide the suction of a liquid or gaseous medium from the isolated interior and being specific to the mammal hollow organ having different physiological features, thereby preventing an excessive negative pressure from being produced in the isolated interior that would otherwise result in suction of a tissue of the mammal hollow organ into the functional opening and, therefore, would result in damage to the hollow organ tissue. Besides, the controlled negative pressure having a level required to provide the suction of the liquid or gaseous medium from the isolated interior and being specific to the mammal hollow organ further contributes to the above mentioned further technical effect, namely increased reliability of the catheter.

Furthermore, the catheter according to the second aspect of the present invention provides a second new technical effect which is improved utility of the catheter. The second new technical effect is further provided by the catheter according to the second aspect of the present invention due to the fact that the projections enclosing the functional opening positioned therebetween are provided between the balloons, and the enclosing projections are ring-shaped. In particular, the improved utility of the catheter is provided due to the fact that possibilities of production of the controlled negative pressure in the isolated interior of the mammal hollow organ, the negative pressure having a level required to provide the suction, are essentially expanded, wherein such expanded possibilities are conditioned by an increased volume of the isolated interior of the mammal hollow organ, the isolated interior being used for producing the controlled negative pressure therein.

Furthermore, the catheter according to the second aspect of the present invention provides a third new technical effect which is the appropriate centering of the functional opening in relation to a target zone of the mammal hollow organ, the target zone being used for sucking a liquid or gaseous medium therefrom. In particular, the third new technical effect is further provided by the catheter according to the second aspect of the present invention due to the fact that the projections enclosing the functional opening positioned therebetween are provided between the balloons, and the enclosing projections are ring-shaped.

According to one embodiment of the present invention according to the second aspect, the catheter may further comprise a net or enclosure being permeable to a liquid medium and/or gaseous medium, the net or enclosure at least partly enclosing a catheter body part defined by the balloons so as to cover the functional opening.

Use of the net or enclosure being permeable to a liquid medium and/or gaseous medium for covering the functional opening in the catheter according to the second aspect of the present invention contributes to the above technical effects which are improved safety and increased reliability of the catheter, in particular due to prevented suction of the hollow organ tissue into the functional opening.

According to another embodiment of the present invention according to the second aspect, the net or enclosure may be attached to the balloons such that the net or enclosure may become strained when the balloons are inflated.

Use of the enclosure attached to the balloons, the enclosure becoming strained between the balloons when inflating the balloons in the catheter according to the second aspect of the present invention also contributes to the above technical effects which are improved safety and increased reliability of the catheter, in particular due to prevented suction of the tissue of the hollow organ into the functional opening of the catheter.

According to other embodiments of the present invention according to the second aspect, the net or enclosure may enclose the balloons such that the net or enclosure may become strained when the balloons are inflated.

Use of the enclosure enclosing the balloons and becoming strained between the balloons when inflating the balloons in the catheter according to the second aspect of the present invention also contributes to the above technical effects which are improved safety and increased reliability of the catheter, in particular due to prevented suction of the tissue of the hollow organ into the functional opening of the catheter.

According to some embodiments of the present invention according to the second aspect, the net or enclosure may be secured on the ring-shaped projections.

Use of the enclosure secured on the ring-shaped projections, the enclosure becoming strained between the balloons when inflating the balloons, in the catheter according to the second aspect of the present invention further contributes to the above technical effects which are improved safety and increased reliability of the catheter, in particular due to prevented suction of the tissue of the hollow organ into the functional opening of the catheter.

According to some other embodiments of the present invention according to the second aspect, the catheter further comprises an inflation channel extending in the catheter body to deliver a liquid or gaseous medium to the balloons to provide inflation thereof.

According to various embodiments of the present invention according to the second aspect, the catheter may further comprise a second channel extending in the catheter body, the second channel being hermetically isolated from the functional channel and the inflation channel, wherein the second channel may be provided at opposite ends thereof with an inlet and an outlet which are provided both in the catheter body outside the catheter body part defined by the balloons, and wherein the second channel is designed to supply a liquid thereto and further provided with an additional outlet, the additional outlet being provided at a catheter distal end used for inserting the catheter into the lumen of the mammal hollow organ.

To achieve the objective of the present invention, as embodied and broadly described herein, in a third aspect of the present invention, there is provided a catheter for isolating an interior of a mammal hollow organ, the catheter comprising: (i) an elongate catheter body designed to be inserted into a lumen of the mammal hollow organ; (ii) two balloons, individually and separately disposed along the catheter body and designed to be inflated to isolate the interior of the mammal hollow organ therebetween; and (iii) a functional channel extending in the catheter body and comprising a functional opening provided in the catheter body between the balloons, wherein the functional channel is designed to allow: (a) a negative pressure to be produced in the isolated interior to take a liquid or gaseous medium therefrom via the functional opening or (b) a liquid or gaseous medium to be supplied into the isolated interior via the functional opening, and wherein the functional opening is positioned between two ring-shaped enclosing projections provided on a catheter body part defined by the balloons, and wherein the catheter body is further provided with a net or enclosure being permeable to a liquid medium and/or gaseous medium, and wherein the net or enclosure at least partly encloses the catheter body part defined by the balloons so as to cover the functional opening, and wherein the net or enclosure is attached to the balloons or encloses them such that the net or enclosure becomes strained when the balloons are inflated.

The catheter according to the third aspect of the present invention provides all the technical effects mentioned above for the catheter according to the first aspect of the present invention and all the technical effects mentioned above for the second aspect of the present invention. In particular, in the catheter according to the third aspect of the present invention, suction of the hollow organ tissue into the functional opening is prevented due to the fact that the functional opening provided in the catheter body is between the ring-shaped projections enclosing the functional opening. In other words, in the catheter according to the third aspect, the ring-shaped projections enclosing the functional opening do not allow the hollow organ tissue to contact the functional opening directly or approach to the functional opening for a distance appropriate for suction of the hollow organ tissue into the functional opening when the negative pressure is produced in the isolated interior between the inflated balloons. Furthermore, in the catheter according to the third aspect of the present invention, suction of the hollow organ tissue into the functional opening is further prevented due to the fact that the net or enclosure in the strained state covers the functional opening and displaces the hollow organ tissue for a predetermined distance away from the functional opening, wherein the prevented suction of the hollow organ tissue into the functional opening of the catheter body allows the safety of the catheter to be improved. Moreover, the safety of the catheter according to the third aspect of the present invention is further improved due to the fact that the net or enclosure in the strained state redistributes the pressure from the inflated balloons on an inner wall of the mammal hollow organ and, therefore, prevents pressure related lesions in the inner wall. Besides, the safety of the catheter according to the third aspect of the present invention is further improved due to the fact that the net or enclosure in the strained state pulverizes or sprays the liquid or gaseous medium be supplied into the isolated interior and, therefore, prevents the inner wall of the mammal hollow organ from being intensively effected by a flow of the supplied liquid or gaseous medium that would otherwise damage the effected inter wall site of the mammal hollow organ. In one embodiment of the present invention according to the third aspect, the catheter may further comprise an inflation channel extending in the catheter body to deliver a liquid or gaseous medium to the balloons to provide inflation thereof.

In another embodiment of the present invention according to the third aspect, the catheter may further comprise a second channel extending in the catheter body and an inflation channel extending in the catheter body to deliver a liquid or gaseous medium to the balloons to provide inflation thereof, wherein the second channel is provided at opposite ends thereof with an inlet and an outlet provided both in the catheter body outside the catheter body part defined by the balloons, and wherein the second channel is hermetically isolated from the functional channel and the inflation channel.

To achieve the objective of the present invention, as embodied and broadly described herein, in a fourth aspect of the present invention, there is provided a system for isolating an interior of a mammal hollow organ, the system comprising: the catheter according to any of the above-described embodiments of the first or second aspect of the present invention; and a functional device connected to the functional channel of the catheter to allow the negative pressure to be produced in the isolated interior to take a liquid or gaseous medium therefrom or a liquid or gaseous medium to be supplied into the isolated interior.

The system according to the fourth aspect of the present invention provides the above-mentioned main technical effect, in particular improves safety of the catheter due to prevented suction of a tissue of the mammal hollow organ into the functional opening of the catheter body that would otherwise cause damage to the hollow organ tissue. In particular, in the present invention according to the fourth aspect of the present invention, suction of the hollow organ tissue into the functional opening is further prevented due to one of the above-described facts: (1) the net or enclosure covering the functional opening is attached to the balloons or encloses them such that the net or enclosure becomes strained when inflating the balloons; (2) the functional opening provided in the catheter body is enclosed by the ring-shaped projections such that the functional opening is between the ring-shaped projections; and (3) the net or enclosure covering the functional opening is attached to the balloons or encloses them such that the net or enclosure becomes strained when inflating the balloons, while the functional opening is positioned between the ring-shaped projections.

BRIEF DESCRIPTION OF THE DRAWINGS

While the specification concludes with claims particularly pointing out and distinctly claiming the present invention, it is believed the same will be better understood from the following description taken in conjunction with the accompanying drawings, which illustrate, in a non-limiting fashion, the best mode presently contemplated for carrying out the present invention, and in which like reference numerals designate like parts throughout the drawings, wherein:

DETAILED DESCRIPTION

Figure 1:
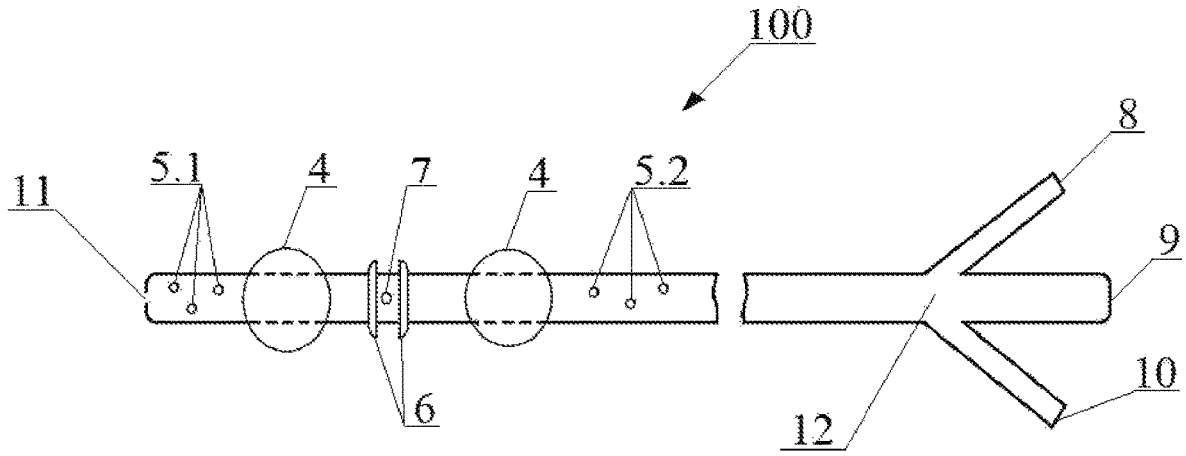
FIG. 1 schematically illustrates a catheter for isolating an interior of a mammal hollow organ according to the present invention.

In the context of this document, unless explicitly stated otherwise, the term "patient" means first of all a potentially sick person (a member of the mammalian class) seeking medical advice or remaining under medical observation to have a disease diagnosed and/or treated, wherein the term "patient" also means potentially sick mammalian animals remaining under medical observation to diagnose and/or treat their disease.

Furthermore, in the context of this document, unless expressly stated otherwise, the term "mammal" means a human or an animal, in particular anthropoid and non-human primates, dogs, cats, horses, camels, donkeys, cows, sheep, pigs, and other well-known mammals.

Furthermore, in the context of this document, unless expressly stated otherwise, the term "user" means any suitably skilled health care professional authorized to insert the catheter according to the present invention into a hollow organ of a mammal (in particular, a human hollow organ), remove the catheter according to the present invention from a hollow organ of a mammal and/or manipulate the catheter according to the present invention inserted into a hollow organ of a mammal, wherein the healthcare professional may be, for example, surgeon, oncologist, endoscopist, thoracic surgeon, angiosurgeon, urologist, veterinarian, etc.

Nowadays, the most advanced method of diagnosing and/or treating inflammatory, autoimmune, infectious, benign and/or malignant diseases occurring in hollow organs, or connected with them organs of a mammal, in particular diseases of pancreas, bile ducts, liver, gastrointestinal tract, and also defects and injuries of hollow organs of a mammal, fistulas, strictures, aneurismal and diverticular dilatations and/or etc., is a liquid biopsy based on the determination of disease-specific features in biological liquids or biological fluids of an organism being specific of a hollow organ or connected with it organs of a mammal. In particular, a liquid biopsy used to diagnose and/or treat pancreatic cancer of a mammal at an initial stage and precancerous transformation is based on the detection of circulating pathologic cells, circulating tumor DNA, RNA, proteins, peptides, metabolites, as well as circulating tumor exosomes in biological liquids of the organism of a mammal (such as blood and pancreatic juice).

One critical aspect of the liquid biopsy is the amount of sampled material, so that it is required to have a sufficient amount of the sampled material to perform the diagnosis. One more critical aspect of liquid biopsy is localization of a disease in a mammalian organism, in particular tumor localization, since pathologic genetic or other diagnostic material isolated from a sample may be typical of cancers of different hollow organs or connected with them organs of a mammal.

In particular, in view of the above reason, to diagnose a cancer, mucinous and intraepithelial neoplasms of the pancreas, pancreatic juice is the most appropriate diagnostic liquid to be used for detecting circulating tumor cells, DNA, RNA, proteins, peptides, metabolites, exosomes therein.

However, sampling of pancreatic juice is the most difficult problem, which is effectively solved by the catheter 100 according to any one of the below-described embodiments of the present invention. Structural and design features and functionalities of the catheter 100 according to the present invention are described in details below in context of solving an illustrative task of collecting pancreatic juice from duodenal papillas, however the scope of the present invention is not limited by them.

It is to note that the minor duodenal papilla and the major duodenal papilla (also referred to in the art as Santorini's papilla and Fateri's papilla, respectively) each represent an anatomical structure in the form of a hemispherical, conical or flattened elevation located at the end of the longitudinal fold of the mucous membrane in the middle of the descending part of the duodenum, in particular about 12-14 cm below the pylorus, wherein in most cases one opening common for the bile and pancreatic ducts is exposed to the duodenum lumen, and in other cases the pancreatic duct is exposed 2-4 cm above the duodenal papilla. A hepato-pancreatic ampoule is located in the duodenal papilla, the ampoule being used for receiving bile and digestive juices of the pancreas and contains the Oddi sphincter regulating the flow of bile or pancreatic juice into the duodenum and preventing the intestinal contents from entering the bile and pancreatic ducts. Therefore, the major duodenal papilla in the duodenum of a mammal is usually 12-14 cm below the pylorus, and the minor duodenal papilla is 2-4 cm above the major duodenal papilla.

In particular, in order to provide the flow of pancreatic juice into the lumen of duodenum it is necessary to create physiological negative pressure around the Fateri's papilla or major duodenal papilla at a level of 40-100 mmH$_2$O, which is normally achieved by peristalsis of duodenum (Physiology of digestion. S. Teesalu. 1987. Tartu. Tartu State University. p. 84; The pancreas. Third edition. 2018. Blackwell. UK. 1300). Another criterion is the need for isolated sampling of a pancreatic juice with inactive digestive enzymes, without gastric and duodenal juice and contents, since presence of gastric and duodenal juice and contents results in activation of enzymes and digestion of cells, DNA, RNA, proteins, peptides, metabolites, exosomes necessary for diagnosis.

FIGS. 1-4 schematically illustrate a catheter 100 for isolating an interior of a mammal hollow organ according to the present invention, wherein the catheter 100 is a catheter to be inserted by a user into a lumen of the mammal hollow organ, and wherein a catheter housing or a catheter body of the catheter 100 is formed as a flexible hollow tube (i.e. has an elongated form) having dimensions, in particular a length and a thickness, suitable for user-assisted insertion or advancement of the catheter 100 within the lumen of the mammal hollow organ towards a placement site. A user manipulating the catheter 100 may be an appropriately skilled healthcare professional, such as, for example, surgeon, oncologist, endoscopist, thoracic surgeon, angiosurgeon, urologist, veterinarian, etc. The catheter 100 of FIG. 1 may be used for any patient, in particular any human or animal (i.e. any mammal).

The catheter 100 of FIG. 1 is provided at its distal end with an axial opening 11, the distal end being used for administering or inserting the catheter 100 into a mammal body followed by advancing the catheter 100 to a placement site within the lumen of the mammal hollow organ, in particular within the lumen of in the gastrointestinal tract, bile ducts, respiratory tracts, urinary system, mammal vessels, a cavity related to uterine and vagina, etc. Furthermore, the catheter 100 is fitted with a three-way connector 12 at its proximal end opposite to the distal end of the catheter 100, wherein the proximal end is located outside of the mammal body when the catheter 100 is inserted into the lumen of the mammal hollow organ. For example, when the catheter 100 is used for isolating an interior of a mammal duodenum, the catheter 100 is administered or inserted by its distal end into a mammal nasal passage followed by advancing the inserted catheter 100 along the mammal duodenum to a placement site in the mammal duodenum.

As shown in FIG. 1, the three-way connector 12 in the catheter 100 may be a pipe or a tube provided with three branches or terminals: a central terminal 9, and two side terminals 8 and 10 hermetically isolated from the central terminal 9, wherein terminals 8, 9, 10 are each provided with a corresponding opening at their free end and each designed to connect to or join an appropriate functional appliance or device thereto.

The central terminal 9 positioned between the side terminals 8, 10 in the three-way connector 12 is designed to connect to or join an appropriate (first) functional appliance or device thereto, wherein the first functional device may be any device known in the art for supplying a gaseous medium or fluid (not shown), for example an enteral nutrition mixture. The device for supplying a gaseous medium or fluid as connected to the central terminal 9 may be, for example, an injection syringe filled, for example, with an enteral nutrition mixture to provide a mammal organism with basic nutrients, energy, vitamins, macronutrients, micronutrients and/or etc., or a medical dropper filled, for example, with an enteral nutrition mixture, or other devices and appliances, including automated or semi-automated, suitable to connect the central terminal 9 thereto and supply a gaseous medium or fluid, for example an enteral nutrition mixture, to the central terminal 9. Therefore, the device for supplying a gaseous medium or fluid connected or attached to the central terminal 9 may be used to provide, for example, nutrition support or clinical nutrition to the mammal body when the catheter 100 is inserted within the lumen of duodenum (or other part of gastrointestinal tract). Furthermore, the device for supplying a liquid or gaseous medium, when connected or attached to the central terminal 9, may be used, for example, to sanitize the stomach and mammal duodenum.

The side terminal 8 being one of the two side terminals in the three-way connector 12 is designed to connect or attach to an appropriate (second) functional appliance or device thereto, wherein the second functional device may be implemented, for example, as a medical suction apparatus, an aspiration device or an aspirator (not shown) comprising of a storage reservoir or a storage container (not shown) for collecting biological gaseous medium, biological liquid and/or biological fluid and an air compressor (not shown) for aspirating or evacuating an air or another appropriate gaseous medium. The pressure for aspirating or evacuating the air or another appropriate gaseous medium may be adjusted by a one skilled in the art for corresponding hollow organs on the basis of information disclosed in the prior art documents, for example, in U.S. Pat. No. 6,712,798.

Furthermore, the second functional device to be attached to the side terminal 8 in the three-way connector 12 may be formed as a special device or device for supplying a gaseous medium or fluid (for example, medical products), for example an injection syringe filled with a liquid to be supplied, or a medical dropper filled with a liquid to be supplied, or other devices or appliances, including automated or semi-automated, suitable for connecting the side terminal 8 thereto and supplying said gaseous medium or fluid to the side terminal 8.

The other side terminal 10 in the three-way connector 12 is designed to connect or attach to an appropriate (third) functional appliance or device thereto, wherein the third functional device may be implemented as a special device or a device for supplying a liquid or gaseous medium under pressure (not shown), for example water or air, in particular an injection syringe filled with a liquid or gaseous medium (for example, water or air) to be supplied, or a medical dropper filled with a liquid (for example, water) to be supplied, or other devices and appliances, including automated or semi-automated, suitable for connecting the side terminal 10 thereto and supplying a fluid or gaseous medium to the side terminal 10.

It is to note that the above-described first functional device (not shown) connectable to the central terminal 9 of the catheter 100 for supplying a liquid, for example a enteral nutrition mixture, and the above-described second functional device (not shown) connectable to the side terminal 8 of the catheter 100 for sampling a biological fluid or biological gaseous medium or supplying a liquid or gaseous medium, and/or the third functional device (not shown) connectable to the side terminal 10 of the catheter 100 for supplying a liquid, for example water, in combination with the catheter 100 shown in FIGS. 1-4 may form a system for isolating an interior of a mammal hollow organ (not shown), which may be used for sampling a biological fluid or biological gaseous medium (for example, a biological liquid) being specific of certain hollow organ of a mammal, or may constitute corresponding parts of such a system. In particular, the above system may be used for isolating an interior in the duodenum of a mammal for sampling pancreatic juice and/or bile.

Furthermore, as shown in FIGS. 1-4, the catheter body of the catheter 100 is provided at its external side with two isolating balloons 4, each being formed as an expanding or inflating soft reservoir, wherein the isolating balloons 4 are spaced at a predetermined distance from each other and from the distal end of the catheter 100. A functional orifice or a functional opening 7 is provided between the isolating balloons 4 in the catheter body of the catheter 100. When the catheter 100 is inserted into the lumen of the mammal hollow organ, one of the isolating balloons 4, namely the farthest from the distal end of the catheter 100, becomes positioned farther than the area of interest in the mammal hollow organ, and the other isolating balloon 4 becomes isolated up to the area of interest in the hollow organ, wherein the functional opening 7 is opposite to the area of interest or next thereto, for example opposite or adjacent to one of the minor and major duodenal papillas, between the minor duodenal papilla and the major duodenal papilla, opposite or adjacent to an intestinal fistula, opposite or adjacent to a wall injury, opposite or adjacent to a tumor, etc.

Furthermore, the catheter 100 for isolating an interior of a mammal hollow organ comprises three separate functional channels provided in the catheter body of the catheter 100: a main channel 1, a supply channel 2 for supplying a liquid or gaseous medium to the isolating balloons 4, the supply channel 2 being hermetically isolated from the main channel 1 and having holes, the holes being provided in the catheter body and each being opened into the interior of corresponding one of the isolating balloons 4, and a functional channel 3 separated from the supply channel 2 and hermetically isolated from the main channel 1. The supply channel 2 and the functional channel 3 extend within a part of the main channel 1 along its length.

The main channel 1 extending substantially along all the length of the catheter 100 communicates with the central terminal 9 of the three-way connector 12, wherein the main channel 1 has an inlet hole or an inlet corresponding to an opening provided in the central terminal 9 at the proximal end of the catheter 100 and also has an outlet hole or an outlet corresponding to the axial hole 11 at the distal end of the catheter 100. When the catheter 100 is inserted into the lumen of the mammal hollow organ, the inlet of the main channel 1 is located outside of the mammal body and communicates with an ambient atmosphere or environment, and the outlet of the main channel 1 communicates with the lumen of the mammal hollow organ, for example esophagus, stomach and duodenum, small intestine or large intestine, and also respiratory tracts, biliary tract, urinary tracts, vessels, etc. Therefore, in case when the above-described first functional device (not shown) is connected to the central terminal 9 of the three-way connector 12, medical products, in particular enteral or parenteral nutrition mixtures, may be initially supplied under pressure from the first functional device to the central terminal 9 through the hole made therein, then supplied from the central terminal 9 to the main channel 1, and finally supplied from the main channel 1 to the interior of the mammal hollow organ through the axial hole 11 shown in FIG. 1.

Figure 2:
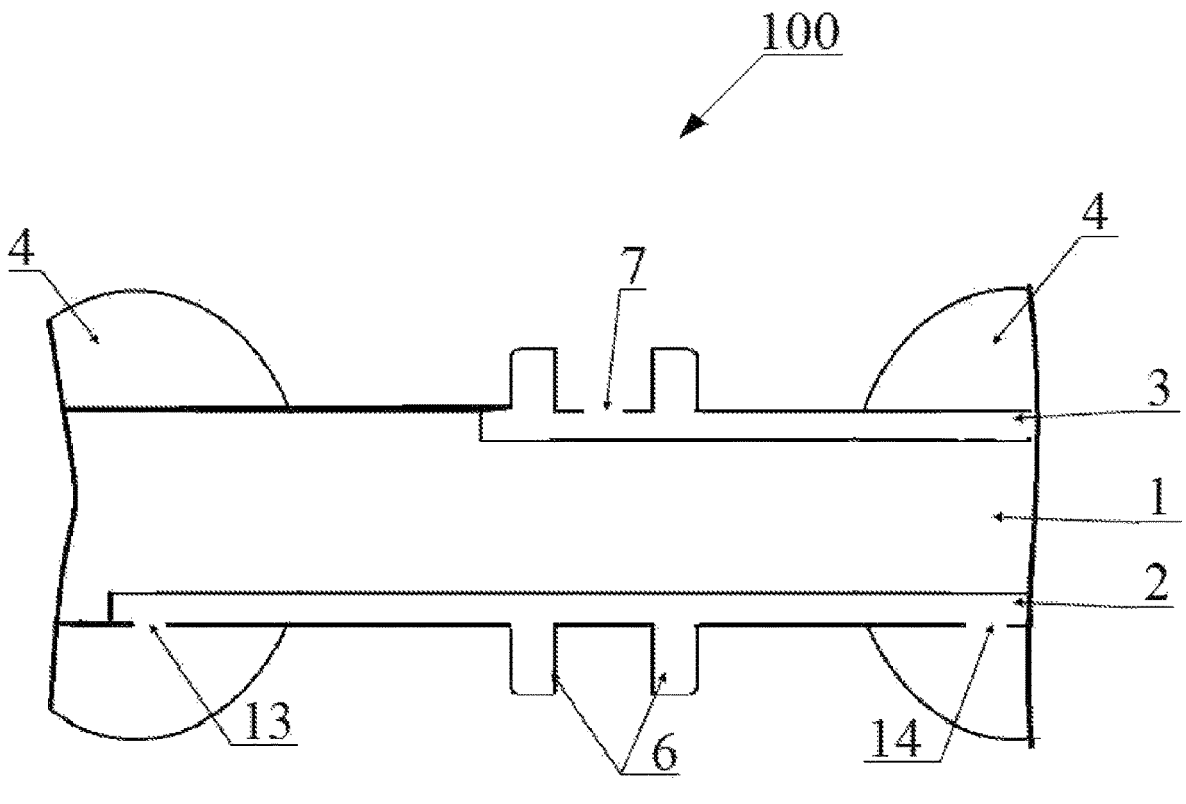
FIG. 2 illustrates a functional opening provided in a catheter body part of the catheter of FIG. 1.

The supply channel 2 extending substantially along a part of the length of the catheter 100 communicates with each of the isolating balloons 4 through one of the corresponding outlets 13, 14 provided in the catheter body of the catheter 100 (as shown in FIG. 2) and communicates with the side terminal 10 of the three-way connector 12, wherein the supply channel 2 has an inlet hole or an inlet corresponding to an opening provided in the side terminal 10 at the proximal end of the catheter 100. When the catheter 100 is inserted into the lumen of the mammal hollow organ, the inlet of the supply channel 2 is located outside of the mammal body to communicate with an ambient atmosphere or environment. Therefore, in case when the above-described second functional device (not shown) is connected to the side terminal 10 of the three-way connector 12, a gaseous medium or fluid, for example a air or water, in a given volume may be firstly supplied under pressure from the second functional device to the side terminal 10 through the hole made therein, then supplied from the side terminal 10 to the supply channel 2, and finally supplied from the supply channel 2 to both the isolating balloons 4 through the corresponding holes made in the catheter body, so that the isolating balloons 4 are inflated or filled with water or a gas by using, in particular, the supply channel 2 of the catheter 100 to provide collectively filled or inflated balloons 4 each having an increased size or volume. The pressure used for filling or inflating the isolating balloons 4 with a fluid or gas for any particular mammal hollow organ may be selected by one skilled in the art on the basis of information disclosed in prior art documents, for example, in U.S. Pat. No. 7,722,568.

It is to note that an increase in size or volume of the isolating balloons 4 can result in bilateral obturation or blockage of the lumen of the mammal hollow organ, for example the lumen of the mammal duodenum where the catheter 100 is inserted, thereby allowing a part of the catheter 100 with a functional opening 7 to be isolated between the inflated isolating balloons 4 in the mammal hollow organ. Therefore, the inflated isolating balloons 4 allow a section of the mammal hollow organ, for example major and minor duodenal papillas of the duodenum, aneurysm, a wall defect of the mammal hollow organ, etc., to be isolated from proximal and distal sections of the mammal hollow organ and, therefore, they exclude or prevent the targeted biological liquid from mixing with other biological liquids and allow the catheter 100 to be fixed within the lumen of the mammal hollow organ, for example within the lumen of the mammal duodenum, due to close adjoining of the isolating balloons 4 by their external sides to an inner wall surface of the mammal hollow organ. In particular, in case when the catheter 100 is inserted into the lumen of duodenum, the inflated isolating balloons 4 allow the minor duodenal papilla and/or the major duodenal papilla of the mammal duodenum to be isolated from proximal and distal sections of the gastrointestinal tract and, therefore prevent mixing of the target biological liquid, wherein the target biological liquid may be a mixture of pancreatic juice and bile, with other biological liquids, such as gastric juice and contents and/or duodenal contents. This ensures that digestive enzymes contained in pancreatic juice remain inactive.

In one embodiment of the present invention, the isolating balloons 4 may communicate therebetween through the supply channel 2, thereby ensuring uniform redistribution of a liquid or gaseous medium used to expand or inflate them, for example, during the passage of a peristaltic wave of the intestine or esophagus. In another embodiment of the present invention, the isolating balloons 4 may be formed, for example, as self-inflating balloons or balloons inflated by air supplied to the supply channel 2 of the catheter 100 through the hole in the side terminal 10 of the three-way connector 12, or balloons inflated in any other way known in the art.

In one of the embodiments of the present invention, the side terminal 10 in the three-way connector 12 may be optionally equipped with a manually operated shut-off valve (not shown) to prevent the backflow or escape of a gaseous medium or fluid, in particular a gas or water located in the isolating balloons 4, the supply channel 2 and the side terminal 10. It is to further note that the isolation valve may be used by a catheter user to adjust an inflation degree of the isolating balloons 4, wherein the user may visually control the inflation degree by using an endoscope. In particular the user may reduce sizes or volumes of the inflated isolating balloons 4 by deflecting or venting a gaseous medium or fluid, in particular a gas or water, from the supply channel 2 by manually opening the check valve.

The functional channel 3 extending substantially along a part of the length of the catheter 100 communicates with the side terminal 8 of the three-way connector 12, wherein the functional channel 3 has an inlet or an inlet port corresponding to the functional opening 7, and an outlet or an outlet port corresponding to an opening provided in the side terminal 8 at the proximal end of the catheter 100. Therefore, in case when the above-described third functional device (not shown) implemented as an aspirator is connected to the side terminal 8 of the three-way connector 12, the functional channel 3 will substantially serve as an aspiration channel, and the functional opening will substantially serve as an aspiration opening, wherein a negative air pressure or a negative air medium pressure will be produced or supported in the interior of the mammal hollow organ, the interior being isolated by the inflated isolating balloons 4, as described above. The negative pressure (also referred to in the art as a technical vacuum) produced in the isolated interior of the mammal hollow organ promotes the evacuation or removal of biological gaseous medium or biological fluid, in particular biological liquid, such as bile and pancreatic juice or pancreatic secretion or pus, or blood, or bronchial secretion, to firstly evacuate said gaseous medium or fluid from the isolated interior to the functional channel 3 through the functional opening 7, then from a functional channel 3 to the side terminal 8, and finally from the side terminal 8 to a storage container of the aspirator through the corresponding hole made in the side terminal 8. It is to note that the functional channel 3 with a functional opening 7 may be used not only for sampling a biological gaseous medium or biological fluid being specific to a particular mammal hollow organ, but also for supplying a required fluid or gaseous medium, for example a drug in a liquid or gaseous form or coloring agent, to the isolated interior in case when the above-described third functional device (not shown) is implemented as a device for supplying a gaseous medium or fluid, for example a medical syringe or medical dropper, is connected to the side terminal 8 of the three-way connector 12.

It is to note that the aspirator being one of possible implementations of the above-described third functional device connectable to the side terminal 8 of the three-way connector 12, when activated by the user, activates an air compressor being a part of the aspirator. The activated air compressor provides aspiration or evacuation of air medium or air from the interior of the mammal hollow organ, for example from the interior of the mammal duodenum isolated by the inflated isolating balloons 4 in the above-described manner, and from an available space in the aspirator storage container, the available space being not filled with a biological gaseous medium or biological fluid (for example, a biological fluid, such as a bile and a pancreatic juice, or a pancreatic secretion) to produce a negative pressure in the isolated interior of the mammal hollow organ, for example in the lumen of the mammal duodenum, thereby taking the biological medium through the functional opening 7 and removing or supplying the taken biological medium, by the functional channel 3, to the storage container for accumulating or collecting therein for a predetermined time period.

It is to note that in one of the embodiments the side terminal 8 of the three-way connector 12 may be used for administering therethrough a liquid or gaseous substance carried by the functional channel 3 and entering the interior between the isolating balloons 4 through the functional opening 7. The administered gaseous or liquid substance, for example a drug or coloring agent, may affect the interior of the mammal hollow organ, the interior being isolated by the isolating balloons 4, and have a diagnostic and/or therapeutic effect thereon.

In one of the embodiments of the present invention, only the above-mentioned supply channel 2 for supplying a fluid (for example, water) to the isolating balloons 4 communicating with the above-described side terminal 10 and the above-described functional channel 3 communicating with the above-described side terminal 8 may be provided in the catheter body.

Furthermore, the catheter body of the catheter 100 is provided at its external side with two generally identical ring-shaped projections 6, each having a radius which is more than that of the body of the catheter 100 or less than that of any one of the inflated isolating balloons 4, wherein each of the ring-shaped projections 6 is located along a length of the catheter body of the catheter 100 on one side in relation to the functional opening 7 next or close thereto, and wherein the ring-shaped projections 6 are preferably equally spaced in relation to the functional opening 7 between the isolating balloons 4. It is to note that in case when the catheter 100 is inserted into the lumen of the mammal hollow organ, and ring-shaped projections 6 serving substantially as projecting sides enclosing the functional opening 7 prevent the functional opening 7 from being contacted with or from approaching a mucosal tissue of the mammal hollow organ for a distance appropriate for suction of the mucosal tissue into the functional opening 7 when an aspirator connected to the functional channel 3 of the catheter 100 is activated by the user and, therefore, when the negative pressure is provided by the aspirator within the isolated interior in the lumen of the mammal hollow organ that would damage the mucosal tissue of the mammal hollow organ. In one embodiment of the present invention, the ring-shaped projections 6 may have any other form different from the ring-shaped form provided that such a form prevents the functional opening 7 from being contacted with the mucosal tissue of the mammal hollow organ or prevents the functional opening 7 from approaching the mucosal tissue of the mammal hollow organ for a distance appropriate for suction of the mucosa into the functional opening 7 when producing a negative pressure in the isolated interior of the mammal hollow organ, the isolated interior communicating with the functional opening 7.

Figure 3:
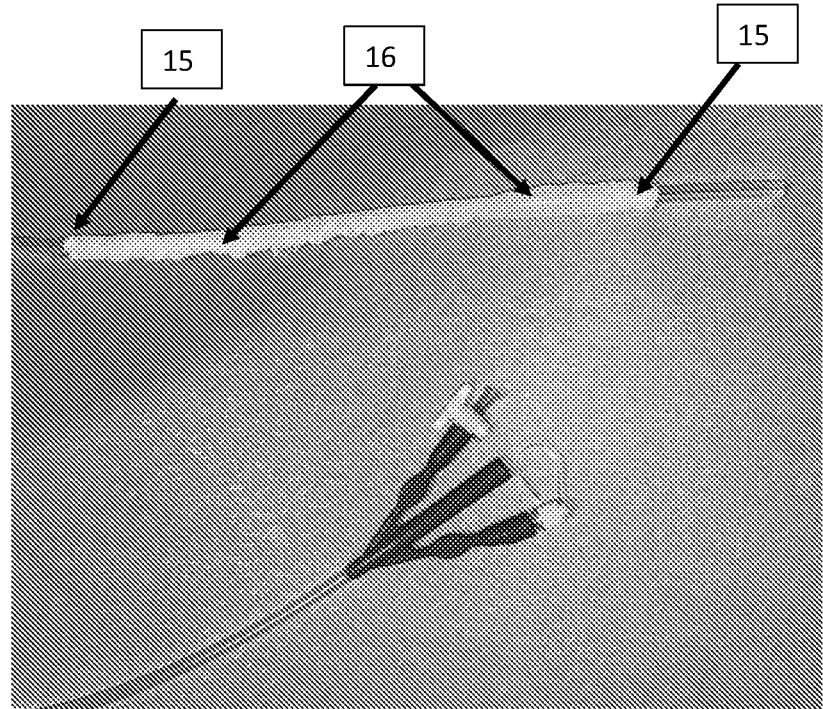
FIG. 3 illustrates the catheter with a grid enclosure in a state when isolating balloons are deflated or blown off.
Figure 4:
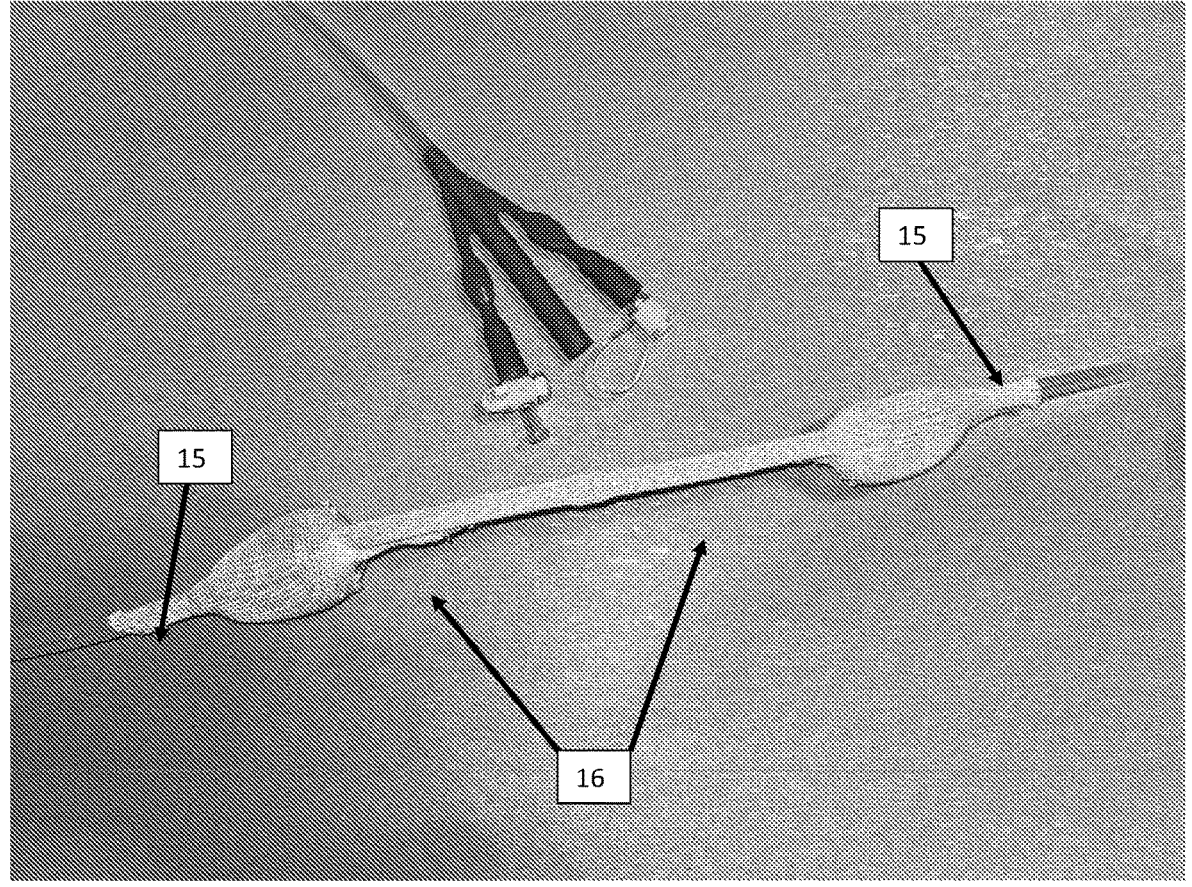
FIG. 4 illustrates the catheter with the grid enclosure in a state when isolating balloons are inflated.

Furthermore, as shown in FIGS. 3-4, the catheter body of the catheter 100 is provided at its external side with two ring-shaped projections 15, wherein each of the ring-shaped projections 15 is provided outside a catheter body part defined by the isolating balloons 4 at a predetermined distance from a corresponding one of the isolating balloons 4, wherein an elastic net or a grid enclosure 16 is attached to the ring-shaped projections 15 to completely or at least partly cover both the isolating balloons 4 and a catheter body part of the catheter 100, the catheter body part being defined by the isolating balloons 4, thereby completely or at least partly enveloping or covering the functional opening 7. When the isolating balloons 4 are inflated, as shown in FIG. 4, the grid enclosure 16 becomes strained or stretched, thereby moving or displacing the inner wall tissue of the mammal hollow organ for a predetermined distance away from the functional opening 7. The grid enclosure 16 in a completely or at least partly strained state forms an elastic outer casing or frame which completely or at least partly encloses the catheter body part defined by the isolating balloons 4 or located between the isolating balloons 4, thereby completely or at least partly enveloping or covering the functional opening 7. The outer frame formed by the grid enclosure 16 has a cylindrical shape and is penetrable by a liquid due to its cellular structure, thereby allowing the biological fluid specific of a certain hollow organ of a mammal to penetrate or pass through a material of the grid enclosure 16 and to enter the functional opening 7. In particular, in case when an aspirating device (not shown) is connected to the side terminal 8 to provide, by the functional channel 3 and the functional opening 7 in the catheter 100, a negative pressure in the isolated interior between the isolating balloons 4, the stretched or strained grid enclosure 16 will hinder glueing or adhesion of the inner wall tissue of the mammal hollow organ (for example, vessel walls, bowel mucosa, bronchus, stomach, ureter, or etc.) to the functional opening 7, thereby allowing the constant aspiration of biological material or biological fluid, for example, bile, pancreatic juice, bronchial secretions, etc., into the container of the aspirating device.

In one embodiment of the present invention, the grid enclosure 16 may be attached to both the isolating balloons 4 such that it completely or at least partly encloses the catheter body part defined by the isolating balloons 4 or located between the isolating balloons 4, thereby completely or at least partly enveloping or covering the functional opening 7. As shown in FIG. 4, when the isolating balloons 4 are inflated, the grid enclosure 16 becomes strained or stretched, thereby allowing for removal or offsetting of the inner wall tissue of the mammal hollow organ for a predetermined distance away from the functional opening 7.

In another embodiment of the present invention, the grid enclosure 16 may be formed as a net-like material or a net preliminary secured in a strained state or at least partly strained state on the ring-shaped projections 6 such that it completely or at least partly encloses a catheter body part defined by the isolating balloons 4 or located between the isolating balloons 4, thereby completely or at least partly enveloping or covering the functional opening 7.

In some other embodiments of the present invention, the grid enclosure 16 may be secured, any suitable fastening means known in the art, in a preliminary strained state on the catheter body of the catheter 100 such that it completely or at least partly encloses the catheter body part defined by the isolating balloons 4 or located between the isolating balloons 4, thereby completely or at least partly enveloping or covering the functional opening 7.

In other embodiments of the present invention, the grid enclosure 16 may have any form allowing the grid enclosure 16 to be secured on the catheter body of the catheter 100, secured on the ring-shaped projections 6 or secured on the isolating balloons 4 to completely or at least partly envelop or cover the functional opening 7.

Furthermore, three auxiliary holes 5.1, 5.2 are provided in the elongate body outside of the isolating balloons 4 and, therefore, outside of the catheter body part provided with the functional opening 7 and defined by the isolating balloons 4. When the catheter 100 is inserted into the lumen of the mammal hollow organ, the auxiliary holes 5.2 positioned further from the distal end of the catheter 100 serve as inlets, and the auxiliary holes 5.1 positioned closer to the distal end of the catheter 100 serve as outlets. It is to note that the auxiliary holes 5.1, 5.2 allow a hollow organ contents, for example air, urine, blood, gastric or intestinal contents with inactive digestive ferments, to pass to distal sections of the mammal hollow organ without entering the interior isolated between the inflated isolating balloons 4 of the catheter 100, thereby preventing or eliminating the formation of congestive and/or inflammatory processes in the mammal hollow organ that could be caused, in particular, by accumulation of blood, urine, air, mucus and other contents in the mammal hollow organ outside of the inflated isolating balloon 4 positioned farther or farthest from the distal end of the catheter 100.

Depending on the use of the catheter 100 according to the present invention and on anatomical parameters of the mammal hollow organ, a length and a diameter of the catheter 100, a wall thickness of the catheter 100, a location and diameter of the isolating balloons 4 in the catheter 100, and a location of the auxiliary holes 5.1, 5.2 may vary. One skilled in the art can easily adjust any parameter of the catheter 100 depending on dimensions of a particular mammal hollow organ.

The thickness of the channels of the catheter 100 and the size of the isolating balloons 4 may be adjusted by one skilled in the art on the basis of information disclosed in the art, for example, U.S. Pat. Nos. 9,526,874, 6,692,465, 5,843, 050, 5,919,163, international publication WO 2009/035581, U.S. Pat. Nos. 5,397,305, 8,398,589, 7,722,568, 6,712,798, 6,638,245, 1,009,865 and/or other prior art information sources.

The length of the catheter 100, a distance between the isolating balloons 4, and a distance from the isolating balloons 4 to the distal end may be matched by one skilled in the art on the basis of information disclosed in the art, for example, U.S. Pat. Nos. 5,314,409, 5,658,264, US patent application No. 20150150572, U.S. Pat. Nos. 5,843,050, 5,397,305, 7,070,606, 6,712,798, 1,009,865 and/or other prior art information sources.

For example, in one of the preferable embodiments of the present invention, the catheter 100 may be implemented as a pancreato-digestive catheter and may have a length of 130 cm. In the present embodiment of the present invention, the isolating balloons 4 are correspondingly spaced at 15 sm and 25 sm from the distal end of the catheter 100, the distal end being used for inserting the catheter 100 into the gastric cavity and the lumen of the mammal duodenum, so that the expanding or inflating of the isolating balloons 4 allows a duodenum interior having a length of at least 10 cm to be isolated. In the present embodiment of the present invention, the functional opening 7 may be in the middle between the isolating balloons 4, i.e. at a distance of 5 cm from each of the isolating balloons 4 and at a distance of 20 cm from the distal end of the catheter 100.

Use of the catheter 100 is illustratively described above in relation to the mammal duodenum. However the use of the catheter 100 is not limited by the mammal duodenum. Therefore, it is clear for one skilled in the art that the catheter 100 according to any of the above-described embodiments can be similarly inserted into a lumen of any another hollow (tubular) internal organ of a mammal, for example into the esophagus, stomach, duodenum, small intestine, large intestine, respiratory tracts, urinary tracts (urogenital system tracts), veins, arteries, vagina, uterus, uterine (Fallopian) tubes, vertebral canal or any appropriate internal tubular organ of the mammal, the mammal tubular organ being related to a corresponding functional system (an apparatus of organs) of a mammal organism from a group of systems including the following systems: digestive system, respiratory system, urinary and reproductive systems (combined into the genitourinary system or urogenital system), endocrine system, circulatory system and immune system, and skeletal system.

Therefore, when used, the catheter 100 according to the present invention may be inserted by the user into the lumen of the mammal duodenum under control of an endoscope (not shown) or of a radiographic equipment (for example, a fluoroscopy equipment) such that one of the corresponding isolating balloons 4, the farthest from the distal end of the catheter 100, is located in the bulb of the mammal duodenum, wherein the endoscope may be manipulated by the user or endoscopist assisting the user. In particular, it is to note that the insertion process of the catheter 100 into the lumen of the mammal duodenum, the removal process of the catheter 100 from the lumen of the mammal duodenum after sampling a required amount the biological liquid and the aspiration process are atraumatic and do not depend on the anatomical features of both the mammal and neoplasms. It is to note that the isolating balloons 4 are in deflated state when the catheter 100 is inserted by the user into the lumen of the mammal duodenum.

According to one example, the catheter 100 may be preliminary equipped with at least one loop designed to grip it with biopsy forceps. To insert the catheter 100 into the desired placement site in the mammal duodenum the distal end of the catheter 100, well lubricated with vaseline oil, is administered through the nasal passage and advanced to the gastric cavity; then the endoscope is further administered or advanced in parallel with the catheter 100 through the mammal oral cavity to the mammal gastric cavity to capture, by means of the endoscope biopsy forceps, the loop(s) of the catheter 100; finally the captured catheter 100 is guided or advanced along with the endoscope to the mammal duodenum. Subsequently, under control of an endoscope, one of the corresponding isolating balloons 4 of the catheter 100, the farthest from the distal end of the catheter 100, is placed in the bulb of the mammal duodenum.

According to another example, a metal guidewire may be preliminary administered or inserted into the main channel 1 of the catheter 100. To insert the catheter 100 into a desired placement site in the mammal duodenum the distal end of the catheter 100, well lubricated with vaseline oil, is inserted through the nasal passage and then advanced to the gastric cavity by using the metal guidewire of the catheter 100; then the endoscope is inserted or advanced in parallel with the catheter 100 through the mammal oral cavity to the mammal gastric cavity to capture, by means of the endoscope biopsy forceps, a first ligature upon detection of the distal end of the catheter 100 and to press the catheter 100 to the endoscope by pulling up the catheter 100 by using the captured first ligature. Subsequently, the endoscope and the catheter 100 pressed against the endoscope are guided through the pylorus to the mammal duodenum, and one of the corresponding isolating balloons 4 of the catheter 100, the farthest from the distal end of the catheter 100, is placed under control of the endoscope within the bulb of the mammal duodenum.

Then, the user connects or attaches the above-described second functional device (not shown) to the side terminal 10 of the three-way connector 12, wherein the second functional device is intended to supply a liquid or gaseous medium, for example a gas or water, to the supply channel 2 of the catheter 100 in a required amount or volume, in particular water in a volume of 40-70 ml, to allow the expansion and inflation of the isolating balloons 4 to closely adjoin to a mucosal tissue of the duodenum, thereby isolating a required interior of the mammal duodenum containing the major duodenal papilla and the minor duodenal papilla, in particular preventing gastric contents and/or duodenal contents with inactive digestive ferments from entering the isolated interior. In particular, it is to note that results experimentally obtained by the inventors show that 40-70 ml of air is required to sufficiently inflate the isolating balloons 4 to a required size for bilateral obturation or occlusion of the mammal duodenum lumen where the catheter 100 may be inserted, as an illustrative example.

Then, the user joins or connects the above-described third functional device (not shown) implemented as an aspirator to the functional channel 3, wherein aspirator is preliminary configured for a constant or variable operation mode providing a required working pressure depending on a particular task. The aspirator activated by the user allows an air medium or air to be sucked, through the functional opening 7 and the functional channel 3 communicating therewith, from the isolated interior of the mammal duodenum, the isolated interior corresponding to the periampullary zone of the duodenum, thereby producing in the interior negative pressure corresponding to pressure normally created by the peristalsis of the duodenum, in particular a negative pressure of 40-100 mmH2O (9-14 kPa)). The negative pressure provided in the isolated interior of the mammal duodenum allows a biological liquid in the form of pancreatic juice or pancreas secretion in combination with bile to be evacuated or retrieved from the pancreas through the major duodenal papilla and the minor duodenal papilla, thereby removing said biological liquid, through the functional opening 7 and the functional channel 3, from the isolated interior of the mammal duodenum and collecting it in a storage container (not shown) of the aspirator. In some cases, there may be further collected in the container a mucosal secretion of the bile and pancreatic ducts, the mucosal secretion being one of the varieties of the biological liquid being specific of duodenum, and/or some biological contents which would enter the bile and the pancreatic ducts as a result of reflux and would contain liquids produced by the organism, the liquids being specific of human duodenum. Subsequently, the biological liquid collected in the storage container of the functional device (not shown), can be delivered for cytological examination and/or molecular genetic examination or other analyses to evaluate characteristics of a morphological structure of cellular elements of pancreatic secretion, cell elements allowing one to detect or reveal pathologic processes being specific, for example, of intraductal neoplasms, neuroendocrine tumors or pancreatic cancer, and to detect neoplasms at an early stage of development, and to perform differential diagnosis between different types of tumors by determining expressions of specific markers (NKX2, S100P, CEA, EFR3A/B, MUC1, MUC2, MUC5, ANXA1, A2, KRT7, MMP7, MMP9, IGFBP3, PSCA, PRSS2, SHh, KRas, TP53, SMAD4, BRCA1, miRNA 21, and miRNA 155).

Furthermore, after connecting the aspirator to the functional channel 3 or instead of the aspirator, a device for supplying a gaseous medium or fluid (for example, an injection syringe or a medical dropper) may be connected to the functional channel 3, enabling the delivery of a required fluid or gaseous medium, for example a drug in a liquid or gaseous form, to the isolated interior of the mammal duodenum.

It is to note that the catheter 100 according to the present invention may remain in the inserted state for a sufficiently long period of time, for example up to seven days (i.e. up to 168 hours), allowing for the pancreatic secretion to be collected in an appropriate amount for reliable identification and verification of pathologic tumor material, so that it generally improves the efficiency of diagnosis and, therefore, subsequent treatment of pancreatic cancer. Furthermore, prolonged sampling increases the likelihood of detecting pathologic cells and other biomarkers not only for pancreatic cancers, but also for malignant conditions of bile ducts and liver, including cholangiocarcinoma and/or hepatocellular cancer.

It is to further note that stimulation of the secretion of pancreatic juice and bile is not required when the catheter 100 is used, so that biological material collected has true biochemical and physiological profile presenting true functional state of pancreas, liver, bile ducts, contractility of the gallbladder.

If necessary, the excretory function of pancreas may be evaluated by examining a biochemical composition of pancreatic secret collected in the above-described manner in the storage container (not shown) in combination with bile by using the catheter 100 according to the present invention.

Furthermore, a qualitative and quantitative analysis of pancreatic juice and bile allows for a true biochemical profile of both biological materials and a volume of daily secretion to be evaluated, thereby diagnosing functional condition of an organ.

The catheter 100 according to any one of the above-described embodiments of the present invention may be used for diagnosing or monitoring the development of at least one disease selected from a group comprising: gastritis, pancreatitis, pancreatic cancer, bile duct cancer, cholangiocarcinoma, hepatocellular cancer, cholangitis, cholelithiasis, wall defects of a hollow organ wall, autoimmune hepatitis, infectious hepatitis, aneurismal or diverticular protrusions of a hollow organ wall, bleeding to a hollow organ interior, strictures of mammal hollow organs and esophagus neuromuscular disorders, stomach, the duodenum, small intestine and large intestine, bile ducts, urinoexcretory ways and respiratory tracts.

Furthermore, the catheter 100 according to any one of the above-described embodiments of the present invention may be used for treating at least one disease selected from a group comprising: pancreatitis, cholangitis, gastrointestinal wall defects, vascular aneurisms, venous thrombs, ureter defects, respiratory tract defects, gastrointestinal hemorrhages, bleeding from the windpipe (trachea), bronchial bleeding, pulmonary hemorrhage, and uterine bleeding.

Furthermore, the catheter 100 according to any one of the above-described embodiments of the present invention may be used to isolate an interior of a mammal vessel when performing a surgical procedure or performing surgical manipulations, in particular in relation to tissues of an inner wall of the mammal vessel.

In particular, there is a treatment or therapeutic effect achieved by restoring and facilitating the evacuation of bile or of pancreatic juice from the corresponding ducts into duodenum when the catheter 100 is used. The pathogenesis of acute inflammatory diseases, such as pancreatitis and cholangitis, is caused at least in part by the impairment or disruption of the outflow of pancreatic juice and bile, the outflow impairment being caused, in particular, by impaired motility (peristalsis) of duodenum of a mammal, so that the isolated interior with a controllable negative pressure (for example, 40-100 mmH2O) producing aspiration of pancreatic juice and a bile by using the catheter 100 allows one to address this medical problem and, therefore, to contribute to the treatment of the above acute diseases.

Furthermore, when the catheter 100 is used, there is a treatment or therapeutic effect achieved by evacuating contents from an interior pertaining to a wall defect of gastrointestinal tract, so that the isolated interior with a controllable negative pressure (for example, at level 70-100 mm water column), allows one to evacuate all of the biological liquids from a defect area and solve this medical problem and, therefore, to contribute to solving said medical problem of a mammal.

It is clear for one skilled in the art that the catheter 100 according to the present invention may be made of any suitable materials on the basis of information disclosed in the prior art, for example, in U.S. Pat. No. 7,722,568 or U.S. Pat. No. 6,638,245, wherein the catheter 100 may be preferably made of polymeric materials.

EXAMPLES

Example No. 1. A patient No. 1 was admitted with girdle pain in the upper abdomen. Amylase in a blood was 1150 U/L. Results of ultrasound examination were as follows: pancreas was increased in size; the head was 35 mm; the catheter body was 32 mm; the tail was 21 mm; strongly heterogeneous; the contour was blurred; the parapancreatic tissue was edematous; liquids were not detected. The MSCT picture corresponds to acute hydropic pancreatitis. The patient started a therapy according to recommendations of the Russian Society of Surgeons, wherein the catheter 100 according to the present invention was inserted into the patient duodenum for 24 hours, and an active aspiration method was performed. After 24 hours, the level of amylase in a blood dropped to 230 U/L, and the pain syndrome was managed.

Example No. 2. A patient No. 2 was admitted with a clinical picture of obstructive jaundice. The examination revealed an increased level of leukocytes up to 14.1×109, wherein a total bilirubin was 145 mmol/L, and a direct bilirubin was 113.2 mmol/L. Amylase in a blood was 57 U/L, alanine aminotransferase (ALT) was 391 U/L, and aspartate aminotransferase (AST) was 90 U/L. Results of ultrasound were as follows: multiple calculi up to 1.3 cm in diameter were detected in a gallbladder, and bile ducts were dilated up to 11 mm. Results of magnetic resonance imaging (MRI) were as follows: a shadow corresponding to a calculus of 6 mm was detected in the distal section of the common bile duct. Results of endoscopic retrograde cholangiopancreatography (ERCP) were as follows: a single 8 mm calculus was identified, and then the identified calculus was endoscopically removed. To prevent the acute pancreatitis the catheter 100 according to the present invention was inserted into a patient duodenum for 24 hours, and an active aspiration method was performed. In the postoperative period, the level of amylase in a blood did not increase more than 87 U/L.

Example No. 3. A patient No. 3 was admitted routinely for examination and treatment. Previously performed MSCT allowed the formation of an anomalous body in pancreas to be detected. Endoscopic ultrasound allowed the formation of an anomalous body having the size of 2 cm by 3 cm to be detected, while a fine-needle biopsy was technically impossible. To selectively sample a pancreatic juice, the catheter 100 according to the present invention was inserted into a patient duodenum. Adenocarcinoma cells and mutations in driver genes, exosomes and protein markers were detected in the sampled pancreatic juice thanks to cytological and molecular examinations.

Example No. 4. A patient No. 4 was admitted with a clinical picture of obstructive jaundice. Results of MRI: a block at the level of confluence of the lobar right and left hepatic ducts was revealed, wherein the block corresponds to the Klatskin tumor of type HA. The catheter 100 according to the present invention was inserted into the patient duodenum, and active aspiration was performed. Abnormal cells and markers of malignant neoplasms were detected in the obtained bile thanks to cytological and molecular examinations.

Example No. 5. Patient No. 5 was diagnosed with chronic pancreatitis. Despite the gastroenterologist's therapy and prescribed enzymatic drugs taken by the patient, body mass reduction, defecation disorders, and diarrhea were observed. To evaluate the functional state of pancreas the catheter 100 according to the present invention was inserted into the patient duodenum for 24 hours, and an active aspiration was performed for obtaining a pancreatic juice. As a result of a biochemical test performed on the obtained pancreatic juice, decreased levels of alpha amylase and lipase were revealed, and also a decrease in the daily excretion of pancreatic juice and bile was revealed. As a result, the dose of enzymatic drugs taken by the patient was increased, and ursodeoxycholic acid drugs and bile substitutes were additionally prescribed.

Example No. 6. A patient No. 6 with jaundice was admitted to an infectious diseases clinic in the city. Results of physical examination showed an enlarged liver, wherein results of a biochemical blood test showed the following: total bilirubin was 329 mmol/L, direct bilirubin was 141 mmol/L, ALT was 1040 U/L, AST was 804 U/L. Serological analysis of blood for HCV antigens, HBsAg was negative. The catheter 100 according to the present invention was inserted into the patient, wherein 100 ml of bile was obtained as a result of active aspiration, and a high copy number of the HCV virus was detected by PCR analysis of bile.

Example No. 7. A patient No. 7 was treated in an infectious diseases clinic for the verified viral hepatitis. After the course of interferons, a repeated PCR analysis of blood did not reveal an active viral process. The catheter 100 according to the present invention was inserted into the patient, wherein 200 ml of bile was obtained as a result of active aspiration, and the PCR analysis of the bile obtained showed an ongoing viral process, so that the scheme and duration of therapy were changed.

Example No. 8. A patient No. 8 was diagnosed with intestinal fistula and peritonitis. The operation, sanitation and drainage of the abdominal cavity were performed on an emergency basis. In order to isolate an intestinal wall defect, reduce its contact with intestinal contents, improve the healing process, and also to provide an additional modality for treating peritonitis by separating abdominal cavity and pathological substrate, the catheter 100 according to the present invention was inserted into an interior related to an intestinal injury such that the isolating balloons 4 were located above and below the injury. After inflating the isolating balloons 4, the isolated interior was produced, and another channel was connected to a suction apparatus to provide sanitization of the interior related to the intestinal fistula to facilitate defect healing. Enteral nutrition was also administered to the patient through the catheter 100.

Example No. 9. A patient No. 9 with girdle pain in the abdomen was admitted to the hospital as an emergency. Based on the results of examination, the patient was diagnosed with acute pancreatitis, of moderate severity, according to the Atlanta classification. At the time of admission, the amylase level was 1320 U/L. The catheter 100 according to the present invention was inserted into the patient, wherein the functional channel 3 was connected to a pump for producing a controllable negative pressure, while enteral nutrition and medical products were administered to the patients through the same catheter 100. As a result, the dynamics of biochemical parameters became positive in accordance with the BISAP scale within 24 hours, and the patient recovered after 7 days.

Example No. 10. A patient No. 10 was admitted to the hospital as an emergency with pain in the right hypochondrium, hectic form of fever and periodic yellowing of the skin. The anamnesis showed that 3 months before the current hospitalization the patient underwent endoscopic manipulation in relation to the bile ducts in order to remove calculus from them. Ultrasound, MSCT showed no changes in the liver, ducts or the presence of abscesses. In order to diagnose cholangitis, the catheter 100 according to the present invention was inserted into the patient, and 50.0 ml of bile was sampled and subjected to bacteriological examination. As a result, the abundant growth of *Klebsiella* spp. was revealed, and its sensitivity to antibacterial drugs was determined. After the selection of pathognomonic antibiotic therapy, the cholangitis symptoms disappeared, and the patient was discharged for an outpatient treatment.

Example No. 11. Patient No. 11 underwent sigmoid colon resection due to the presence of a mass lesion. It was revealed during intestine mobilization that a formation invaded all the layers of intestine, wherein there was regional lymphadenopathy with involvement of retroperitoneal tissue. When mobilizing the intestine with a tumor, communication was established with the injured ureter of the left kidney. Urologists were called in the operating room and treated surgically the defect of the ureter. To prevent complications, an adjusted in size catheter 100 according to the present invention was administered retrogradely along a guide wire, and one of the isolating balloons 4 was inflated in the pelvis of the left kidney, and the other isolating balloon 4 (the lower isolating balloon) was inflated in the bladder, wherein the functional channel 3 was connected to a suction apparatus for producing a controllable negative pressure. The catheter 100 was removed in 14 days, wherein the excretory function of the left kidney was not impaired. The patient was discharged for outpatient treatment.

Example No. 12. A patient No. 12 with a pulmonary hemorrhage was admitted. Bronchoscopy revealed a putrescent bleeding tumor of the right main bronchus. For the purpose of hemostasis and preservation of bronchial patency, and also for the prevention of lung atelectasis, catheter 100 according to the present invention was administered into the right bronchus. The catheter 100 according to the present invention was inserted such that the tumor was between the isolating balloons 4, wherein inflation of the isolating balloons 4 stopped the blood flowing to other parts of the bronchus. To stop the bleeding a hemostatic agent was administered through the functional channel 3 of the catheter 100. As a result, there was no relapse of the bleeding for three (3) days of observation. The catheter 100 according to the present invention was subsequently removed. The patient was discharged for outpatient treatment ten (10) days later.

Example No. 13. A patient No. 13 with an instrumentally confirmed clinic of mediasthenitis was admitted on an emergency basis. The examination revealed an esophagus defect due to necrosis caused by a piece of meat. For treating the esophagus, the catheter 100 for isolating an interior of a mammal hollow organ according to the present invention was inserted. The isolating balloons 4 of the catheter 100 were inflated to isolate the defect, and the functional channel 3 was connected to a suction apparatus to provide a controllable negative pressure. As a result, the patient was discharged for outpatient treatment after 1.5 months.

Example No. 14. A patient No. 14 with headaches and general cerebral symptoms was admitted on an emergency basis. MSCT with intravenous contrast enhancement revealed an aneurysm in the basin of the right middle cerebral artery with signs of extrusion. The patient was taken to the angiographic operating room, wherein the catheter 100 according to the present invention was administered through the femoral approach. Positioning of the catheter 100 was performed under control of fluoroscopy such that an interior of the aneurysm was isolated by the isolating balloons 4, wherein the functional channel 3 was opposite the aneurysm. A filling solution filling the aneurysm cavity was administered through the functional channel 3. After the necessary exposure, the catheter 100 allowed to maintain a circumferential blood flow. Subsequently the catheter 100 was removed. The patient was discharged from a hospital in 21 days.

Example No. 15. A patient No. 15 was admitted routinely for surgical treatment of pancreatic cancer. An examination showed a head tumor invading the inferior vena cava. To reduce blood loss the catheter 100 according to the present invention was inserted into the vein, and the isolating balloons 4 were inflated above and below the pancreas head tumor, thereby shunting blood and returning blood to the heart. During the resection of the gland, a section of the inferior vena cava was resected with autoplasty of the saphenous vein of the lower extremity. The blood loss was 500 ml. Therefore, optimal temporary and physiological conditions were created both for the patient and surgeons.

Example No. 16. A patient No. 16 was admitted for surgical treatment of sigmoid colon cancer. In a postoperative period, the patient developed colo-rectoanastomosis failure for ⅓ of the circumference. To treat the colon the catheter 100 according to the present invention was retrogradely inserted into the rectum such that one of the isolating balloons 4 of the catheter 100 was positioned most proximally in relation to the defect, and the other isolating balloon 4 of the catheter 100 was positioned most distally in relation to the defect. When the isolating balloons 4 of the catheter 100 were inflated, an interior related to the defect was isolated from other sections of the large intestine. Due to the main channel, proximal sections of the bowel were cleaned with water. As a result, the defect was closed in 3 weeks.

Example No. 17. A patient No. 17 was admitted with suspected liver tumor. To perform a liquid biopsy the catheter 100 according to the present invention was inserted; an interior related to the major and minor duodenal papillas was isolated by the isolating balloons 4 of the catheter 100, and aspiration of bile started. When the catheter 100 was removed, a bile aspirate was delivered for genetic and cytological examination, wherein no pathologic markers and cells were detected. When the bile aspirate is taken, the grid enclosure 16 covering the isolating balloons 4 of the catheter 100 was removed and washed with a buffer solution, whereupon the water was collected, and a cell sediment was obtained after centrifugation. Cytological examination of the obtained cell sediment allowed the presence of hepatocellular cancer cells to be revealed.

Example No. 18. A patient No. 18 was admitted on an emergency basis with a uterine bleeding. A colposcopy allowed a putrescent cervical cancer to be revealed. To stop the bleeding, the catheter 100 was inserted into a vaginal and uterine cavity, and an interior related to a tumor area was isolated by the isolating balloons 4 of the catheter 100. The instillation with a hemostatic drug was performed for the tumor through the functional channel of the catheter 100. The bleeding was stopped, and the patient left a hospital.

Therefore, the above-described catheter 100 allows functional investigations of any mammal hollow organ to be conducted or performed, and also allows appropriate treatments to be performed. Furthermore, the examination and/or laboratory analysis of a biological liquid collected by the catheter 100 allows inflammatory formations, benign formations and malignant growth, and also infectious diseases to be differentially diagnosed with a high accuracy. The catheter 100 allows inflammatory diseases, bleeding and defects of walls of the mammal hollow organ to be treated by evacuating a specific liquid. The isolated interior providing a bypass function during a surgical manipulation allows a hemostasis to be controlled, and also allows surgical manipulations to be performed, in particular allows the resection of a vessel site to be performed and also allows a plastic surgery of the resected vessel site to be performed. It is to further note that the catheter 100 according to the present invention or the above-described system according to the present invention, the system comprising the catheter 100 according to the present invention, allows a high volume of a biological material in a normal physiological and biochemical state to be collected without any additional stimulation of an excretory function of the mammal hollow organ, in particular due to the production of the negative pressure corresponding to a physiological negative pressure, the physiological negative pressure being produced, for example, due to the peristalsis of the intestine in the isolated interior of the mammal hollow organ having the catheter 100 inserted into the lumen thereof.

33

The invention claimed is:

1. A catheter (100) for isolating an interior of a mammal hollow organ, the catheter comprising:

an elongate catheter body designed to be inserted into a lumen of the mammal hollow organ;

two balloons (4), individually and separately disposed along the catheter body and designed to be inflated to isolate the interior of the mammal hollow organ therebetween; and a functional channel (3) extending in the catheter body and comprising a functional opening (7) provided in the catheter body between the balloons (4), wherein the functional channel (3) is designed to allow:

a negative pressure to be produced in the isolated interior to take a liquid or gaseous medium therefrom via the functional opening (7); or a liquid or gaseous medium to be supplied into the isolated interior via the functional opening (7), characterized in that the catheter body is further provided with a net or enclosure (16) being permeable to a liquid medium and/or a gaseous medium, wherein the net or enclosure (16) at least partly encloses a catheter body part defined by the balloons (4) so as to cover the functional opening (7), and wherein the net or enclosure (16) is attached to the balloons (4) or encloses them such that the net or enclosure (16) becomes strained when the balloons (4) are inflated.

2. The catheter (100) of claim 1, further comprising an inflation channel (2) extending in the catheter body to deliver a liquid or gaseous medium to the balloons (4) to provide inflation thereof.

3. The catheter (100) of claim 2, further comprising a main channel (1) extending in the catheter body, the main channel (1) being hermetically isolated from the functional channel (3) and the inflation channel (2), wherein the main channel (1) provided at opposite ends thereof with an inlet (5.2) and an outlet (5.1) which are provided both in the catheter body outside the catheter body part defined by the balloons (4), and wherein the main channel (1) is designed to supply a liquid thereto and further provided with an additional outlet (11), the additional outlet (11) being provided at a catheter distal end used for inserting the catheter (100) into the lumen of the mammal hollow organ.

4. The catheter (100) of claim 2, wherein each of the functional channel (3) and the inflation channel (2) are hermetically isolated from each other.

5. The catheter (100) of claim 1, wherein two ring-shaped projections (6) enclosing the functional opening (7) are further provided on the catheter body between the balloons (4) such that the functional opening (7) is between the two ring-shaped projections (6) and adjacent thereto.

6. A catheter (100) for isolating an interior of a mammal hollow organ, the catheter comprising:

an elongate catheter body designed to be inserted into a lumen of the mammal hollow organ;

two balloons (4), individually and separately disposed along the catheter body and designed to be inflated to isolate the interior of the mammal hollow organ therebetween; and a functional channel (3) extending in the catheter body and comprising a functional opening (7) provided in the catheter body between the balloons (4), wherein the functional channel (3) is designed to allow:

a negative pressure to be produced in the isolated interior to take a liquid or gaseous medium therefrom via the functional opening (7) or

a liquid or gaseous medium to be supplied into the isolated interior via the functional opening (7), characterized in that two ring-shaped projections (6) enclosing the functional opening (7) are further provided on the catheter body between the balloons (4), such that the functional opening (7) is between the two ring-shaped projections (6), wherein the two ring-shaped projections each have a radius being less than that of the inflated balloons (4), wherein the two ring-shaped projections (6) are both designed such that they allow a distance between a mucosal tissue of the mammal hollow organ, the mucosal tissue being between the inflated balloons (4).

7. The catheter (100) of claim 6, further comprising a net or enclosure (16) being permeable to a liquid medium and/or gaseous medium, the net or enclosure (16) at least partly enclosing a catheter body part defined by the balloons (4) so as to cover the functional opening (7).

8. The catheter (100) of claim 7, wherein the net or enclosure (16) is attached to the balloons (4) such that the net or enclosure (16) becomes strained when the balloons (4) are inflated.

9. The catheter (100) of claim 7, wherein the net or enclosure (16) encloses the balloons (4) such that the net or enclosure (16) becomes strained when the balloons (4) are inflated.

10. The catheter (100) of claim 7, wherein the net or enclosure (16) is further secured on the ring-shaped projections (6).

11. The catheter (100) of claim 6, further comprising an inflation channel (2) extending in the catheter body to deliver a liquid or gaseous medium to the balloons (4) to provide inflation thereof.

12. The catheter (100) of claim 11, further comprising a main channel (1) extending in the catheter body, the main channel (1) being hermetically isolated from the functional channel (3) and the inflation channel (2), wherein the main channel (1) is provided at opposite ends thereof with an inlet (5.2) and an outlet (5.1) which are provided both in the catheter body outside a catheter part defined by the balloons (4), and wherein the main channel (1) is designed to supply a liquid thereto and further provided with an additional outlet (11), the additional outlet (11) being provided at a catheter distal end used for inserting the catheter (100) into the lumen of the mammal hollow organ.

13. A catheter (100) for isolating an interior of a mammal hollow organ, the catheter comprising:

an elongate catheter body designed to be inserted into a lumen of the mammal hollow organ;

two balloons (4), individually and separately disposed along the catheter body and designed to be inflated to isolate the interior of the mammal hollow organ therebetween; and a functional channel (3) extending in the catheter body and comprising a functional opening (7) provided in the catheter body between the balloons (4), wherein the functional channel (3) is designed to allow:

a negative pressure to be produced in the isolated interior to take a liquid or gaseous medium therefrom via the functional opening (7); or a liquid or gaseous medium to be supplied into the isolated interior via the functional opening (7);

characterized in that the functional opening (7) is positioned between two ring-shaped enclosing projections (6) provided on a catheter body part defined by the balloons (4), and the catheter body is further provided with a net or enclosure (16) being permeable to a liquid medium and/or a gaseous medium, wherein the net or enclosure (16) at least partly encloses the catheter body part defined by the balloons (4) so as to cover the functional opening (7), and wherein the net or enclosure (16) is attached to the balloons (4) or encloses them such that the net or enclosure (16) becomes strained when the balloons (4) are inflated.

14. The catheter (100) of claim 13, further comprising an inflation channel (2) extending in the catheter body to deliver a liquid or gaseous medium to the balloons (4) to provide inflation thereof.

15. The catheter (100) of claim 14, further comprising a main channel (1) extending in the catheter body and an inflation channel (2) extending in the catheter body to deliver a liquid or gaseous medium to the balloons (4) to provide inflation thereof, wherein the main channel (1) is provided at opposite ends thereof with an inlet (5.2) and an outlet (5.1) provided both in the catheter body outside the catheter body part defined by the balloons (4), and wherein the main channel (1) is hermetically isolated from the functional channel (3) and the inflation channel (2).

16. A system for isolating an interior of a mammal hollow organ, the system comprising:
the catheter (100) of claim 1; and
a functional device connected to the functional channel (3) to allow the negative pressure to be produced in the isolated interior of the mammal hollow organ to take the liquid or gaseous medium therefrom via the functional opening (7) or allow a liquid or gaseous medium to be supplied into the isolated interior via the functional opening (7).

17. A system for isolating an interior of a mammal hollow organ, the system comprising:
the catheter (100) of claim 6; and
a functional device connected to the functional channel (3) to allow the negative pressure to be produced in the isolated interior of the mammal hollow organ to take the liquid or gaseous medium therefrom via the functional opening (7) or allow a liquid or gaseous medium to be supplied into the isolated interior via the functional opening (7).

18. A system for isolating an interior of a mammal hollow organ, the system comprising:
the catheter (100) of claim 13; and
a functional device connected to the functional channel (3) to allow the negative pressure to be produced in the isolated interior of the mammal hollow organ to take the liquid or gaseous medium therefrom via the functional opening (7) or allow a liquid or gaseous medium to be supplied into the isolated interior via the functional opening (7).

* * * * *